US008722408B2

(12) United States Patent
Yamamura et al.

(10) Patent No.: US 8,722,408 B2
(45) Date of Patent: *May 13, 2014

(54) TRAP VECTORS AND GENE TRAPPING METHOD BY USING THE SAME

(75) Inventors: Ken-ichi Yamamura, Kumamoto (JP); Kimi Araki, Kumamoto (JP)

(73) Assignee: Transgenic Inc., Kumamoto-Shi (JP)

( * ) Notice: Subject to any disclaimer, the term of this patent is extended or adjusted under 35 U.S.C. 154(b) by 154 days.

This patent is subject to a terminal disclaimer.

(21) Appl. No.: 12/987,601

(22) Filed: Jan. 10, 2011

(65) Prior Publication Data
US 2011/0117642 A1    May 19, 2011

Related U.S. Application Data

(62) Division of application No. 11/907,497, filed on Oct. 12, 2007, now abandoned, which is a division of application No. 10/030,658, filed as application No. PCT/JP00/02916 on May 2, 2000, now Pat. No. 7,312,075.

(30) Foreign Application Priority Data
Jul. 14, 1999  (JP) .................................... 11-200997

(51) Int. Cl.
*C12N 15/85* (2006.01)
*C12N 15/63* (2006.01)

(52) U.S. Cl.
USPC ........................ 435/455; 435/320.1; 435/325

(58) Field of Classification Search
None
See application file for complete search history.

(56) References Cited

U.S. PATENT DOCUMENTS

| | | | |
|---|---|---|---|
| 4,237,224 A | 12/1980 | Cohen et al. | |
| 4,468,464 A | 8/1984 | Cohen et al. | |
| 4,736,866 A | 4/1988 | Ledet et al. | |
| 4,736,886 A | 4/1988 | Oike | |
| 4,740,470 A | 4/1988 | Cohen et al. | |
| 4,873,191 A | 10/1989 | Wagner et al. | |
| 4,959,317 A | 9/1990 | Sauer | |
| 5,300,431 A | 4/1994 | Pierce et al. | |
| 5,378,618 A | 1/1995 | Sternberg et al. | |
| 5,464,764 A | 11/1995 | Capecchi et al. | |
| 5,487,992 A | 1/1996 | Capecchi et al. | |
| 5,658,772 A | 8/1997 | Odell et al. | |
| 5,789,215 A | 8/1998 | Berns et al. | |
| 5,851,808 A | 12/1998 | Elledge et al. | |
| 5,928,914 A | 7/1999 | Leboulch et al. | |
| 5,994,620 A | 11/1999 | Schimenti et al. | |
| 6,037,125 A | 3/2000 | Hasty | |
| 6,057,104 A | 5/2000 | Hasty | |
| 6,080,576 A | 6/2000 | Zambrowicz et al. | |
| 6,777,235 B1 | 8/2004 | Ong et al. | |

FOREIGN PATENT DOCUMENTS

| | | | |
|---|---|---|---|
| WO | WO-94/24274 A | 10/1994 | |
| WO | WO-98/14614 A | 4/1998 | |
| WO | WO-98/20030 A | 5/1998 | |
| WO | WO-99/02719 A | 1/1999 | |
| WO | WO-99/07389 A | 2/1999 | |
| WO | WO-99/10479 A | 3/1999 | |
| WO | WO-99/50426 A | 10/1999 | |
| WO | WO-00/09681 A | 2/2000 | |
| WO | WO-00/31236 A | 6/2000 | |

OTHER PUBLICATIONS

Mullins et al. (1996, Clin. Invest. vol. 97, No. 7, 1557-1560).*
Campbell and Wilmut, Theriogenology, 1997. vol. 47, No. 1, pp. 63-69.*
Araki et al.; "Targeted Integration of DNA Using Mutant lox Sites in Embryonic Stem Cells"; Nucleic Acids Research, vol. 25, No. 4, pp. 868-872, (1997).
Araki et al.; "Efficiency of Recombination of CRE Transient Expression in Embryonic Stem Cells: Comparison of Various Promoters"; Journal of Biochemistry, vol. 122, No. 5, pp. 977-982, (1997).
Irmgard et al.; "Selective Disruption of Genes Transiently Induced in Differentiating Mouse Embryonic Stem Cells by Using Gene Trap Mutagenesis Ans Site-Specific Recombination"; Molecular and Cellualr Biology, vol. 18, No. 5, pp. 3081-3088, (1998).
Li et al.; "Generation of Mice With a 200-KB Amyloid Precursor Protein Gene Deletion by CRE Recombinase-Mediated Siste-Specific Recombination in Embryonic Stem Cells"; Proceeding of National Academy of Sciences of the USA, vol. 93, No. 12, pp. 6158-6162, (1996).
Wurst,W. et al., Genetics 139: 889-899,1995.
Chowdhury,K. et al., Nucleic Acids Res. 25:1531-1536, 1997.
Hicks, G. G. et al., Nature Genetics 16: 338-344,1997.
Zambrowicz, B. P. et al., Nature 392: 608-611,1998.
Sauer, B. and Henderson, N. Proc. Natl. Acad. Sci. USA 85: 5166-5170, 1988.
Lakso, M. et al., Proc. Natl. Acad. Sci. USA 89: 6232-6236, 1992.
Gu,H. et al., Independent control of immunoglobulin switch recombination at individual switch regions evidenced 1993.
Albert, H. et al., Plant Journal, vol. 7, No. 4, pp. 649-659, (1995).
Schwenk, F. et al., Nucleic Acids Res. 23: 5080-5081, 1995.
Miyazaki, J. et al., Gene 79: 269-277, 1989.
Niwa, H. et al., Gene 108: 193-200, 1991.
Niwa, H. et al., J. Biochem, 113: 343-349, 1993.
Niwa, H. et al., Gene 169: 197-201, 1996.
Abe, K.,Niwa,H. et al., Exp. Cell Res. 229: 27-34, 1996.
Oike, Y. et al., Human Molecular Genetics, vol. 8, No. 3, pp. 387-396 (1999).
Zambrowicz et al., Int. J. Dev. Biol. vol. 42, pp. 1025-1036, (1998).
Oike et al., Blood, vol. 93, No. 9, pp. 2771-2779, (1999).
Kuhn et al., Immunological Techniques, vol. 9, No. 2, pp. 183-188, (1997).
Araki et al., "Exchangeable Gene Trap Using the CRE/Mutated Lox System," Cellular and Molecular Biology, vol. 45(5), pp. 737-750 (1999).

(Continued)

Primary Examiner — Celine Qian
(74) Attorney, Agent, or Firm — Birch, Stewart, Kolasch & Birch, LLP

(57) ABSTRACT

A trap vector containing a loxP sequence composed of inverted repeat sequence 1, a spacer sequence and inverted repeat sequence 2 in this order, the loxP sequence being a mutant loxP wherein a part of the inverted repeat sequence 1 or 2 is mutated.

4 Claims, 13 Drawing Sheets

(56) References Cited

OTHER PUBLICATIONS

Freidrich et al., Genes & Development, vol. 5, pp. 1513-1523 (1991).
Mullins et al., Clin. Invest., 1996, vol. 97, No. 7, pp. 1557-1560.
Bradley et al., Biotechnology, 1992, vol. 10, pp. 534-539.
Campbell and Wilmut, Theriogenology, 1997, vol. 47, No. 1, pp. 63-72.

* cited by examiner

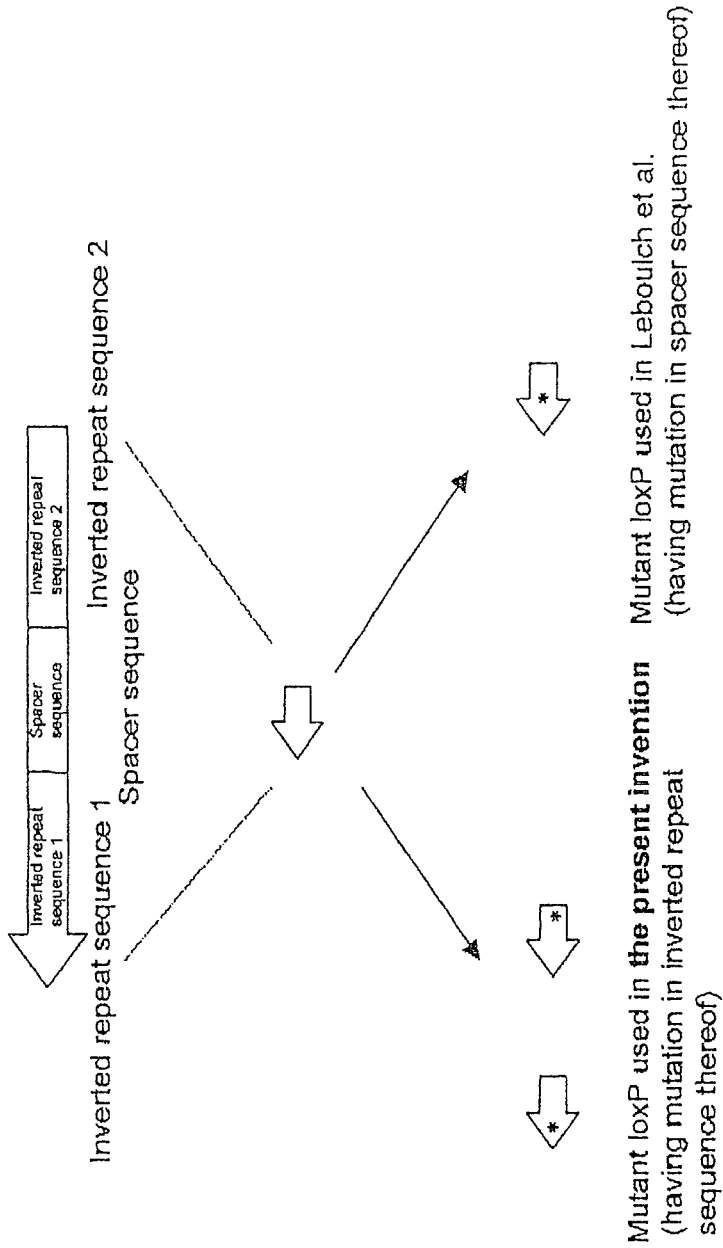
Supplemental Figure 1

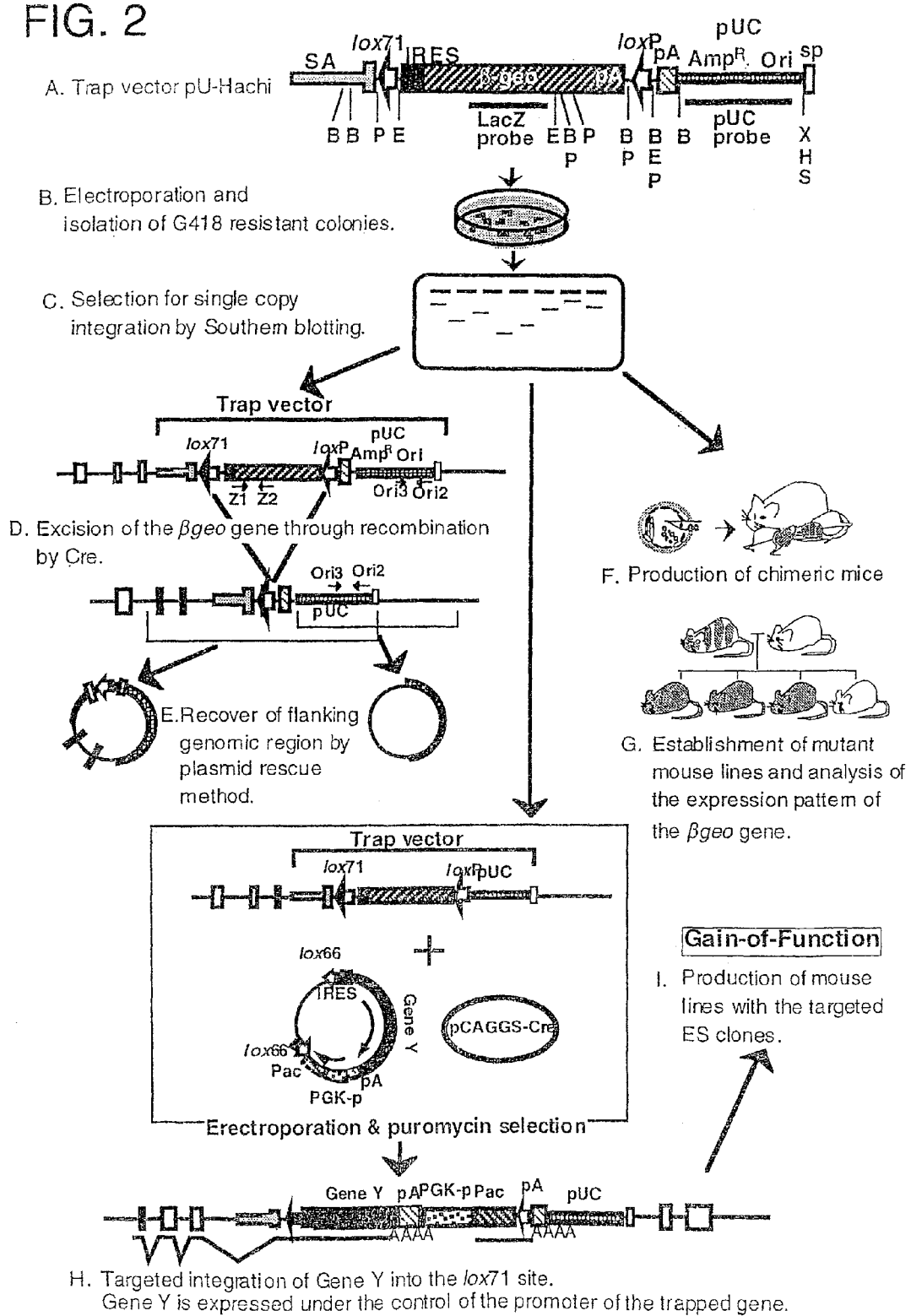

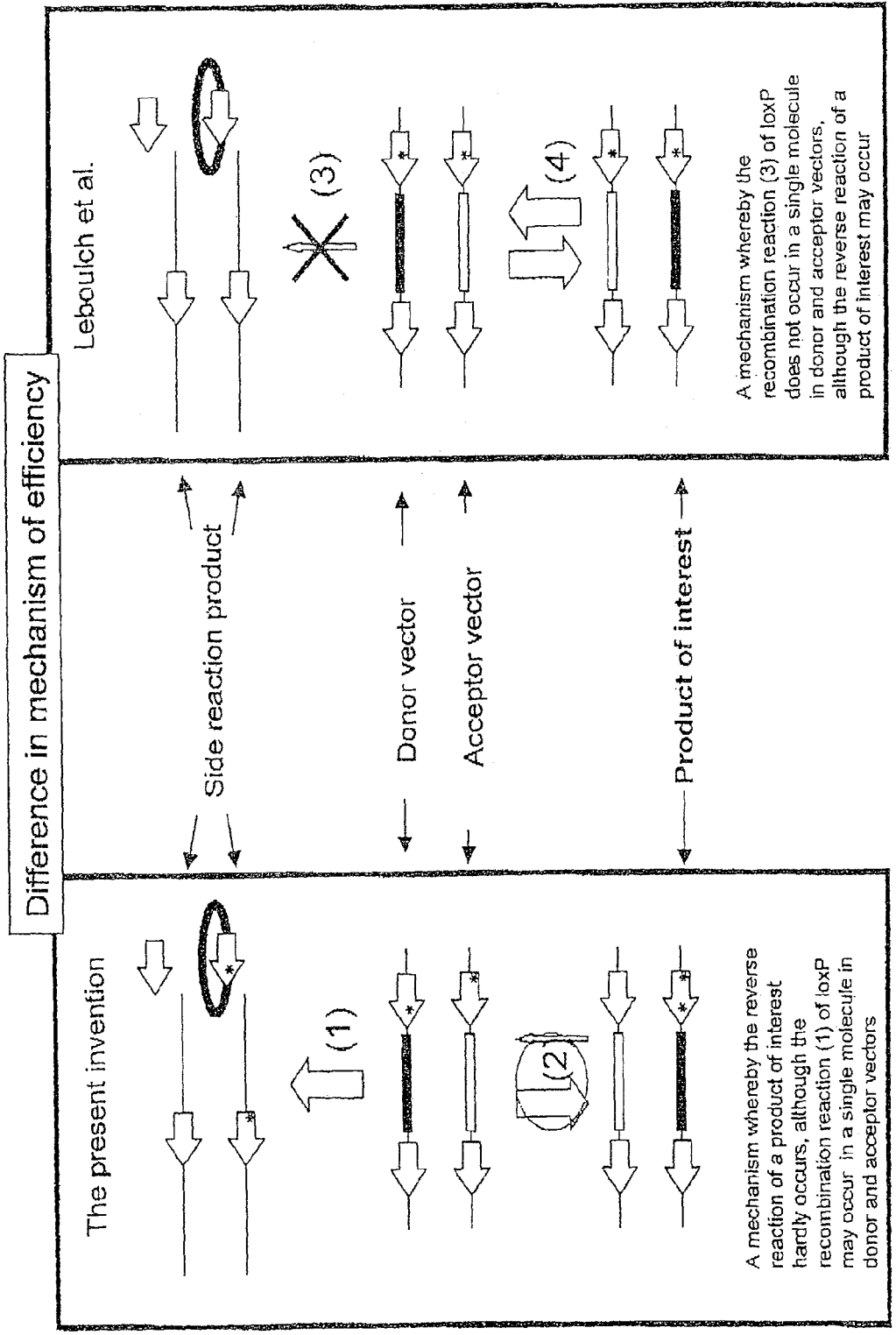
Supplemental Figure 2

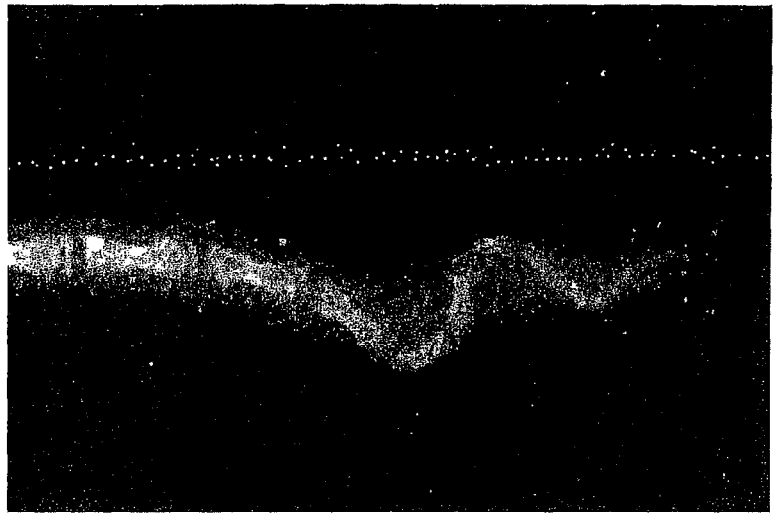
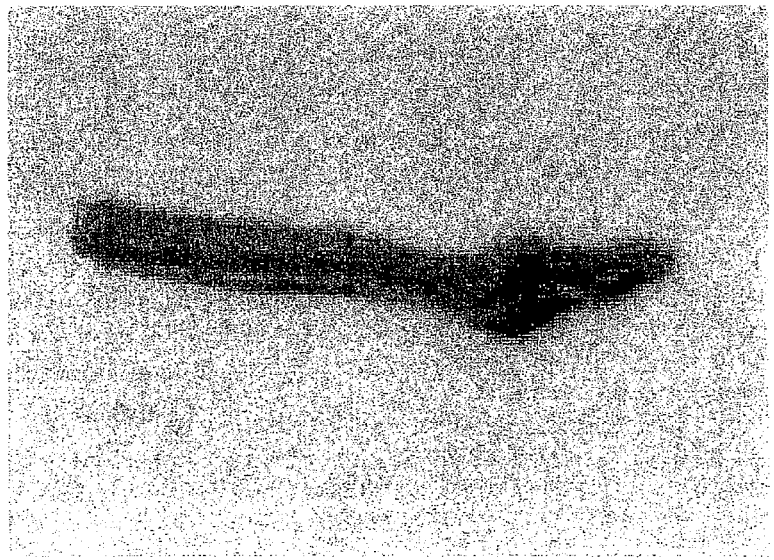
FIG. 11　Abnormality in the tail of Ayu8021

TRAP VECTORS AND GENE TRAPPING METHOD BY USING THE SAME

This application is a Divisional of co-pending U.S. application Ser. No. 11/907,497 filed Oct. 12, 2007, now abandoned U.S. application Ser. No. 11/907,497 is a Divisional of U.S. application Ser. No. 10/030,658 filed on Jan. 11, 2002, now U.S. Pat. No. 7,312,075, which issued on Dec. 25, 2007. U.S. application Ser. No. 10/030,658 is the national stage of PCT International Application No. PCT/JP00/02916 filed on May 2, 2000. PCT International Application No. PCT/JP00/02916 claims the benefit of priority of JP 1999-200997, filed on Jul. 14, 1999. The entire contents of each of the above-identified applications are hereby incorporated by reference.

TECHNICAL FIELD

The present invention relates to random mutation ES clone technology using gene trapping.

BACKGROUND ART

It is said that structural analysis of human genome will be completed in or before 2003 as the human genome project is progressing well. Now, the age of isolating genes one by one and analyzing their structures separately seems to be over, and we have come into the age of "structural analysis" of genome.

With the nucleotide sequence of genome alone, however, information on functions is insufficient. Thus, a novel analysis system for functional analysis is needed. Further, although one of the major goals of human genome analysis is to elucidate causative genes in human diseases, such diseases cannot be explained with the structures of causative genes alone.

Accordingly, production of model individuals is an indispensable assignment in order to analyze processes of disease development and to develop new treatment methods after the identification of causative genes.

On the other hand, if genome is divided into gene regions and non-gene regions in terms of structure, it is considered that these two parts have separate functions and that it is necessary to analyze the functions of both parts (FIG. 1 and Supplemental FIG. 1). From the viewpoint of entire genome, each gene is performing only a part of the entire function. Genome is not a mere collection of genes and may have unknown functions. In fact, a new concept "position effect mutation" has been established. From this, it is presumed that genome has regions of unknown functions.

Gene regions are composed of regulatory regions and coding regions. At present, the target of genome functional analysis is coding regions. When mouse is compared with human, the kinds of genes they have are almost equal. Therefore, functional analysis of the regulatory region is important. There is difference in species between mouse genes and human genes. It is believed that this difference is not due to difference in protein but due to difference in the regulation of gene expression.

The function of a transcription factor or the like involved in the regulation of gene expression can be elucidated from the sequence of the coding region of the relevant gene. The analysis of the functions of those elements to which the transcription factor binds is extremely difficult at present because a number of those elements exist in the regulatory region of one gene. However, as a technique of functional analysis, a method using bacterial artificial chromosomes may be considered.

It is considered that functional analysis of coding regions may be performed at the mRNA level, protein level, cell level, tissue/organ level and individual (i.e. whole animal) level. It is believed that such analysis at the mRNA level can be performed using DNA chips. On the other hand, the use of embryonic stem (ES) cells seems to be the best way for performing functional analysis at other levels, because various cell and tissue derivative systems have been developed directly from ES cells in vitro and a number of such systems are expected to be developed in the future. Furthermore, the use of ES cells is advantageous in that individual level analysis systems can be established.

From the foregoing, it is understood that gene knockout at ES cell level and production of knockout mice in which the relevant genes are knocked out are extremely important in functional analysis of genome.

To date, homologous recombination using ES cells has played a major role in the production of knockout mice. However, considering this method not as a strategy of producing knockout mice separately but from a strategic viewpoint of producing knockout mice comprehensively, this method has serious problems.

First, this method requires too much time. In the production of knockout mice, it is the rate-determining step to isolate knockout ES clones generated through homologous recombination using ES cells. Even a skillful researcher needs at least three months for isolating a knockout ES clone. Thus, only four genes can be knocked out in one year. Accordingly, in the case of introducing each one mutation into $10^5$ genes, 2,500 researchers are required for one year. It is estimated that approximately 1,000 lines of knockout mice are produced in one year in the world. This means that it would take 100 years to produce $10^5$ knockout ES clones. This is so unrealistic compared to the advance in the structural analysis of human genome that is to be completed in 2003.

Secondly, this method requires too much cost. At least 2 to 4 million yen is necessary to produce one line of knockout mouse excluding personnel expenses and depreciation expenses. Thus, production of $10^5$ simple knockout mice requires 200 to 400 billion yen.

As described above, the conventional homologous recombination using ES cells has problems, and genome is vast. However, the number of genes in genome is limited. Thus, it is necessary to isolate from genome those genes having important functions. In many cases, the function of a gene is elucidated only after production of a knockout mouse in which the relevant gene is disrupted. Therefore, knockout mice are directly connected with future development of epoch-making drugs and have extremely high value added. Under circumstances, it has become the world's "strategy" to produce mutant mice at random and in large scale. At present, the three methods described below are considered most reasonable in the production of random mutation mice.

The first one is a method using ethyinitrosourea (ENU), a mutagen. A project of large-scale mutant production using ENU has been started in Europe. In Germany, Dr. Balling of the Institute of Mammalian Genetics and others started this project in 1997 as a part of the human genome project. In England, supported by SmithKline Beecham, Dr. Brown and others started this project at MRC Mouse Genome Center in Harwell aiming at establishment of mutant mice having mutations mainly in brain/nervous system. To date, these two groups have established approximately 200 lines of mutant mice exhibiting dominant inheritance. The project is proceeding more efficiently than expected. In the United States, it has been decided that structural analysis of mouse genome and production of mutant by the ENU method start with a huge budget (6 billion yen/year) at Case Western Reserve University, Oak Ridge National Laboratory, etc.

When ENU is administered to adult male mice, ENU acts on spermatogoniums before meiosis and causes about 50 to 100 point mutations per spermaogonium at random. Mutations occur at a frequency of 1/1,000/gamete per locus. Therefore, by crossing one treated male mouse with one normal female mouse, many kinds of mutant mice can be produced in F1 generation. In the method using ENU, if 1,000 mice are screened for a specific locus, one mouse has a mutation caused in that locus in terms of probability. Thus, this method is considered highly efficient.

The second method is a method using chlorambucil that is also a mutagen. This method causes mutations in spermatogoniums at the same frequency as in the method using ENU. However, these mutations are deletion mutations, and sometimes as many as one megabases may be deleted.

The third method is a method using gene trapping. Gene trapping is a technique that was developed for the purpose of searching for unknown genes by introducing trap vectors containing a marker gene into ES cells and then monitoring the expression of the marker gene. Trap vectors are integrated into ES cells at random and, as a result of their integration, endogenous genes (genes present in cells and tissues inherently) are disrupted in most cases. Therefore, preparing chimeric mice from such ES cells can produce various knockout mice.

However, each of the methods using a mutagen and the method using gene trapping has an advantage(s) and a drawback(s) (Table 1).

TABLE 1

|  | ENU Method | Chlorambucil Method | Gene Trapping |
|---|---|---|---|
| Nature of Mutation | Point mutation | Deletion mutation | Any desired mutation |
| Production of Mutant Mouse | Easy | Easy | Difficult |
| Identification of Mutant Mouse | Difficult | Medium | Easy |
| Other Features |  |  | Can use ES trap clones |

According to the ENU method, production of mutant mice is easy, but establishment of individual mutant lines is not easy because segregation by crossing should be conducted. Further, in order to identify mutated genes, the relevant locus should be identified first by linkage analysis using polymorphic DNA markers, and then the gene should be isolated by positional cloning. Thus, the ENU method requires complicated operations.

According to the chlorambucil method, production of mutant mice is easy, but deleted sites should be identified. For that purpose, analysis must be made using a number of polymorphic DNA markers. Besides, generally, methods using a mutagen such as chlorambucil need large breeding rooms. Thus, such methods require much expenses and labor.

Although the gene trap method requires labor and technology for producing mutant mice, identification of mutated genes is easy and experiments can be conducted according to the size of breeding rooms. Gene trap ES clones per se are precious resource for functional analysis of genome. The gene trap method is also remarkably different from other methods in this point.

Some laboratories in the world have already started production of mutants by gene trapping. In the United States, a private firm Lexicon Genetics Incorporated is undertaking random disruption by gene trapping using retrovirus vectors. However, ordinary researchers can hardly use this service because of the following reasons. Briefly, it is not sure whether an endogenous gene is disrupted or not even if the gene is trapped; it is not clear whether germline chimeric mice can be produced; an additional charge is required for the production of chimeric mice; and considerable charges are required for using the service. In Germany, gene trapping is performed toward a goal of 12,000 clones as a part of the ENU project. Anyway, these are proceeding focusing on the analysis of trapped genes rather than the establishment of mouse lines.

DISCLOSURE OF THE INVENTION

The problem for solution by the invention is to overcome the problems that conventional gene trap methods have, to develop a novel "exchangeable gene trap method" that seems almost ideal, to establish ES trap clones in large scale using the above method, and to produce mouse mutants using the trap clones. Thus, it is an object of the invention to provide trap vectors; a method of gene trapping; transgenic or knock-out animals in which a trapped gene is introduced; and trapped genes.

As a result of intensive and extensive researches toward the solution of the above problems, the present inventors have reached an idea of using the bacteriophage-derived recombination system Cre-loxP in gene trapping. Thus, the present invention has been achieved. Cre is a recombinase that recognizes a loxP sequence and causes recombination at that site.

The present patent application provides the following inventions:

(1) A trap vector containing a loxP sequence composed of inverted repeat sequence 1, a spacer sequence and inverted repeat sequence 2 in this order, the loxP sequence being a mutant loxP wherein a part of inverted repeat sequence 1 or 2 is mutated.

As a specific example of the mutant loxP in which a part of its inverted repeat sequence 1 is mutated, lox71 (e.g. the sequence shown in SEQ ID NO: 1) may be given. As a specific example of the mutant loxP in which a part of its inverted repeat sequence 2 is mutated, lox66 (e.g. the sequence shown in SEQ ID NO: 2) may be given.

(2) A vector generated from recombination between a trap vector containing a mutant loxP wherein a part of inverted repeat sequence 1 is mutated and a the trap vector containing a mutant loxP wherein a part of inverted repeat sequence 2 is mutated.

(3) A trap vector selected from the group consisting of the following (a) to (i):
   (a) SD-SA-lox71-IRES-M-loxP-PV-SP
   (b) SP-lox7-IRES-M-loxP-PV-SP
   (c) SA-lox71-IRES-M-loxP-pA-PV-SP
   (d) SA-lox71-IRES-M-loxP-puro-pA-PV-SP
   (e) lox71-M-loxP-pA-lox2272-PV-lox511
   (f) lox71-IRES-M-loxP-pA-lox2272-PV-lox511
   (g) (lox7'-integrated SA)-M-loxP-pA-lox2272-PV-lox511
   (h) (lox71-integrated SA)-IRES-M-loxP-pA-lox2272-PV-lox511
   (i) (lox71-integrated SA)-M-loxP-pA-lox2272-promoter-M-lox511-SD, wherein SP represents any sequence; SA represents a splice acceptor; SD represents a splice donor; IRES represents an internal ribosomal entry site; M represents a marker gene; puro represents puromycin resistance gene; pA represents a poly(A) sequence; and PV represents a plasmid vector.

In the trap vectors (a) to (i) described above, -geo gene may be given as a specific example of the marker gene, and pBR322, pUC plasmids (pUC18, pUC19, pUC118, pUC119, etc.), pSP plasmids (pSP64, pSP65, pSP73, etc.) and pGEM plasmids (pGEM-3, pGEM-4, pGEM-3Z, etc.) may be enumerated as specific examples of the plasmid vector.

(4) A method of gene trapping comprising introducing any of the above-described trap vectors into embryonic stem cells, and embryonic stem cells into which the trap vector is introduced by the method.

(5) A method for producing a transgenic animal or knockout animal comprising introducing the above-described embryonic stem cells into an animal, and a transgenic animal or knockout animal produced by the method.

As a specific example of the above animal, one selected from the group consisting of mouse, rat, rabbit, guinea pig, pig, sheep and goat may be given.

Hereinbelow, the present invention will be described in detail. The present specification encompasses the contents of the specification and/or drawings of the Japanese Patent Application No. 11-200997 based on which the present application claims priority.

The present invention relates to a method of gene trapping, transgenic or knockout animals into which a trapped gene is introduced, and trapped genes. An outline of the method of gene trapping according to the invention is shown in FIG. 2 and Supplemental FIG. 2. First, in order to achieve the object of the present invention, a trap vector is constructed and introduced into ES cells, followed by isolation and selection of trap clones (FIG. 2A-C). In FIG. 2, pU-Hachi vector is exemplified. Subsequently, chimeric animals (e.g. chimeric mice) are produced, followed by production of mutant mice derived from the trap clone (FIG. 2F-G). On the other hand, using the trapped and selected clone, isolation and sequencing of the trapped gene as well as recovery of the genome by plasmid rescue are performed (FIG. 2C-E). Further, the clone is subjected to electroporation and selection with a drug such as puromycin to thereby trap a gene of interest. Then, the trapped gene is expressed, followed by production of ES clone-derived mouse lines (FIG. 2H-I).

The present invention can be summarized as follows (including pilot studies).

(1) Overall Efficiency (1-1) Screening by Formation of Embryoid Bodies

One hundred and six neomycin resistant clones were suspension-cultured for the formation of embryoid bodies. The expression of -galactosidase was analyzed at the stage of ES cells and after the induction of differentiation. As a result, it was found that 90 trap clones (86%) were expressing -galactosidase at any one of the above stages.

(1-2) Selection of Clones Indicating Single Copy Integration

DNA was extracted from 109 trap clones that had expressed the marker gene during the process of embryoid body formation, and then integration patterns of the trap vector were analyzed. As a result, 75 clones (70%) had a single copy integrated. Of these, 24 clones (22%) were complete (i.e. retained the replication origin of the plasmid) and 40 clones (37%) lacked pUC. Even if pUC was lost, it could be re-inserted by using lox71 site. Therefore, these 64 clones (59%) were found to be useful (Table 4).

(1-3) Efficiency of Germline Chimera Production

Chimeric mice were produced using the above-mentioned trap clones. As a result, germline chimeric mice were obtained from approximately one half of the clones.

(1-4) Summary of the Entire Experiment

It was found that about 26% of the neomycin resistant clones selected initially reached the final stage of the experiment. Since the efficiency of germline chimera production is now increasing, it is believed that the overall efficiency can be increased further. However, the efficiency achieved at this time seems to be sufficient for the practice of researches.

(2) Efficiency of the Gene Trap Method

As a result of the tests so far conducted, 24 trap lined were established. Of these, 13 lines have proceeded to analysis at the gene level. Nucleotide sequences of these lines were compared With GenBank and EMBL databases using BLAST program. The results were as follows: 9 clones individually trapped a known gene; 3 clones individually trapped an EST; and the remaining 1 clone trapped an unknown gene (Table 2). According to the reports so far made by other researchers, 10-25% of trapped genes are known genes; 10-20% are ESTs; 50-80% are unknown genes; and 2-10% are repeats.

TABLE 2

| | Known Gene | EST | Unknown Gene | Repeat |
|---|---|---|---|---|
| Present Invention | 69.2% | 3 (23.1%) | 1 (7.7%) | |
| Previous Reports | 10-25% | 10-20% | 50-80% | 2-10% |

(3) Trapped Genes

The inventors examined whether those genes involved in development and cell growth had been efficiently trapped or not by ascertaining the kinds of known genes by a screening method utilizing formation of embryoid bodies. As a result, it was found that the known genes were CBP (CREB binding protein) and Sp1 that are transcription factors; cyclin 132 involved in cell cycle: Crk and pHPS1-2 involved in signal transduction; rRNA, suil, hnRNP L and RNA polymerase 1; and mitochondrial DNA (Table 3). Thus, it was found that very common genes were trapped. A major part of these genes are involved in cell growth. This suggests that the screening system utilizing formation of embryoid bodies works well.

TABLE 3

| Class | Clone No. | Gene |
|---|---|---|
| ☐☐Nucleus | | |
| (1) Transcription | Ayu3-112 | CBP |
| | Ayu8-038 | Sp1 |
| (2) Cell Cycle | Ayu3-008 | Cyclin B2 |
| | Ayu6-003 | Homologous to the E. coli cell division protein Ftsj1 |
| (3) Signal Transduction | Ayu8-104 | Crk |
| | Ayu8-025 | pHPS$_1$-2 |
| (4) Cell Skeleton | Ayu8-003 | dynamin II |
| ☐☐Cytoplasm | | |
| (1) Translation | Ayu3-022 | rRNA |
| | Ayu8-016 | sui1 |
| | Ayu8-016 | Upstream region of hnRNP L |
| | Ayu8-019 | Very likely to be RNA polymerase 1 |
| (2) Others | Ayu3-001 | Mitochondrial DNA |
| ☐☐Unknown | Ayu7-003 | Unknown |

(4) Confirmation of Gene Disruption by Trapping

It is one of the major points whether endogenous genes have been actually disrupted or not by gene trapping. Thus, the inventors have analyzed the structure of the trap site for 6 known genes. As a result, it was found that the trap vector was inserted into the promoter region in one gene; into an exon in one gene; and into an intron in 4 genes. In all of them, the gene was completely or partially disrupted. Therefore, it has become clear that endogenous genes can be disrupted efficiently by the method of gene trapping of the invention (FIG. 10).

Hereinbelow, the present invention will be described in more detail.

1. Construction of Trap Vectors

Gene trapping is a method for trapping unknown genes on genome utilizing the fact that trap vectors introduced into ES cells are integrated into mouse endogenous genes incidentally and at random. "Gene trapping" means that a trap vector enters into a specific gene on genome and captures that gene. The vector for gene capturing is called "trap vector". Genes have enhancers, promoters, exons, poly(A) sequences, etc. The trap vector is capable of capturing any of them. For this purpose, a trap vector with a structure suitable for the specific capturing may be used.

Generally, exon trap vectors are composed of a reporter gene with a splice acceptor alone, a drug selection marker gene and a plasmid. Only when these vectors are integrated downstream of a mouse endogenous gene, the reporter gene is expressed. This means that it is possible to know the vector's integration into an endogenous gene by monitoring the expression of the reporter gene in the trap vector. If a plasmid such as pUC19 has been linked to the trap vector, the trapped endogenous gene can be isolated by the technique called plasmid rescue. "Plasmid rescue" is a technique for recovering a gene of interest by selection with ampicillin, etc. of those cells transformed with electroporation or the like (FIG. 2E). Furthermore, since the endogenous gene is disrupted at the time of trapping, knockout mice can be produced immediately. Further, since the reporter gene is expressed under the control of the expression regulatory region of the endogenous gene, the tissue specificity and time specificity of the gene can be analyzed easily.

In conventional gene trapping methods, even if a mouse endogenous gene could be disrupted completely, it has been impossible to introduce thereinto subtle mutations, such as single amino acid substitution, seen in human hereditary diseases. Also, it has been impossible to replace the disrupted mouse gene with a human gene. Toward the solution of these problems, the present invention has modified the Cre-loxP system (a bacteriophage-derived recombination system) and utilized it in the trap vector in gene trapping. As a result, it has become possible to insert any gene into a mutant loxP site of the trap vector after a mouse gene has been disrupted as a result of the integration of the trap vector. According to the present invention, it has become possible to introduce subtle mutations, such as single amino acid substitution, seen in human hereditary diseases. It has also become possible to replace the trapped gene with a human gene. The trap vector of the invention may be used for trapping various genes. In particular, it may be used preferably for exon trapping or promoter trapping.

loxP (locus of crossing (X-ing) over, P1) is a 34 bp sequence (5'-ataacttcgtata gcatacat tatacgaagttat-3') (SEQ ID NO: 3). The 13 bases at its 5' end (called "inverted repeat sequence 1") and the 13 bases at its 3' end (called "inverted repeat sequence 2") constitute inverted repeat sequences, which are separated by an 8 bp spacer (gcatacat) (FIG. 3). The term "inverted repeat sequences" used herein means that a sequence located on one side of the spacer is complementary to a sequence located on the other side of the spacer in opposite orientation. In other words, the sense strand of one sequence is homologous to the antisense strand of the other sequence in opposite orientation to each other. These two repeat, sequences have opposite orientation and, when a double-strand is formed, one same sequence is repeated.

Thus, they are called inverted repeat sequences. As shown in FIG. 3, in one strand (for example, the sense strand) of the double-strand, inverted repeat sequence 1 (5'-ataacttcgtata-3'; SEQ ID NO: 4) (the left side in FIG. 3) is complementary, in the 5',3' direction, to inverted repeat sequence 2 (5'-tatacgaagttat-3': SEQ ID NO: 5) (the right side in FIG. 3) in the 3',5' direction.

Unlike ordinary sequences, loxP has directionality. Therefore, when the loxP sequence is represented in the above-mentioned 5',3' direction in the present invention, an arrow pointing the left (e.g. " ") will be included in the representation.

Cre (causes recombination) means a recombinase that causes genetic recombination and, upon recognition of the above-described repeats, cleaves the spacer in such a manner that "cataca" in the spacer is left as a cohesive end (FIG. 3).

In bacteria, recombination occurs between two loxP sites, and insertion or deletion reaction takes place. If it is possible to cause insertion reaction in mammal cells, then any desired gene can be inserted later. This would dramatically expand the applicability of gene trapping. Actually, since mammal cells have large nuclei, circular DNA molecules with once deleted loxP will diffuse and insertion reaction is hardly observed.

Toward the solution of the above problems, the present inventors have elaborated a method in which mutations are introduced into the loxP sequence in order to cause insertion reaction and, once a gene has been inserted into genome, the gene does not undergo deletion (i.e. not removed from the genome). For this method, the inventors have prepared two mutant loxP sequences (FIG. 4).

Briefly, the inventors created one mutant by introducing substitution mutations into one of the inverted repeat sequences of loxP (sense strand)(ATAACTTCGTATA (SEQ ID NO: 4); shown at the left in FIG. 4b) so that the mutated sequence becomes TACCGTTCGTATA (underlined portion was changed). This mutant is designated "lox71" (SEQ ID NO: 1; FIG. 4b). The other mutant was created by introducing substitution mutations into the other inverted repeat sequence of loxP (sense strand) (TATACGAAGTTAT (SEQ ID NO: 5); shown at the right in FIG. 4b) so that the mutated sequence becomes TATACGAACGGTA (underlined portion was changed). This mutant is designated "lox66" (SEQ ID NO: 2; FIG. 4b).

When recombination has occurred between lox71 on genome and lox66 on a plasmid, a loxP sequence having mutations in both repeats (designated "lox71/66"; TACCGTTCGTATA GCATACAT TATACGAACGGTA; SEQ ID NO:6) is located on the 5" side of the inserted DNA (FIG. 4a, see at the left) and a wild-type loxP sequence (ATAACTTCGTATA GCATACAT TATACGAAGTTAT; SEQ ID NO: 3) on the 3' side of the inserted DNA (FIG. 4a, see at the left). As a result, Cre no longer can recognize lox71/66 and thus cannot cause recombination with loxP. In the case of homologous recombination between two wild-type loxP sequences, a circular DNA containing the excised loxP is physically separated. Thus, the reaction tends toward deletion rather than insertion. On the other hand, when lox71 is used on chromosomes and lox66 is used on circular DNA molecules, Cre has difficulty in recognizing the lox71/66 generated as a result of integration of the DNA. Thus, the reaction tends toward insertion rather than deletion, and the inserted state of insertion is maintained (FIG. 5). It should be noted that, in the present invention, lox66 may be used on chromosomes, and lox71 may be used on circular DNA molecules.

Actually, when a mutant loxP (hereinafter, sometimes referred to as "mutant lox") such as lox71 has been integrated into ES cells in advance, and a plasmid containing other mutant loxP (e.g. lox66) is introduced thereinto, the plasmid is integrated into the genome. Therefore, if this lox71, for example, has been integrated into a gene trap vector in advance, it becomes possible to insert any desired gene later by using lox66. Thus, according to the present invention, it has become possible to replace the trapped gene with a gene into which a subtle mutation(s) has (have) been introduced or a human gene.

Gene trap vectors using this mutant lox (lox71 or lox66) may be constructed as described below (see FIG. 6). Here, it should be noted that the following trap vectors are provided only for illustration, not for limitation. Thus, although lox71 is used as an example of a mutant lox in the following vectors, vectors using lox66 instead of lox71 are also included in the present invention.

(a) U8: SP-SA-lox71-IRES-M-pA-loxP-PV-SP
(h) U8delta: SP-lox71-IRES-M-pA-loxP-PV-SP
(c) pU-Hachi: SA-lox71-IRES-M-loxP-pA-PV-SP
(d) pU-12: SA-lox71-IRES-M-loxP-puro-pA-PV-SP
(e) pU-15: lox71-M-loxP-pA-lox2272-PV-lox511
(f) pU-16: lox71-IRES-M-loxP-pA-lox2272-PV-lox511
(g) pU-17: (lox71-integrated SA)-M-loxP-pA-lox2272-PV-lox511
(h) pU-18: (lox71-integrated SA)-IRES-M-loxP-pA-lox2272-PV-lox511
(i) (lox71-integrated SA)-M-loxP-pA-lox2272-promoter-M-lox511-SD In the above-described vector components, SP represents any sequence; SA represents a splice acceptor; SD represents a splice donor; IRES represents an internal ribosomal entry site; M represents a marker gene; puro represents puromycin resistance gene; pA represents a poly(A) sequence; and PV represents a plasmid vector.

When trap vectors are integrated into genomic DNA, a part of the vector is deleted in most cases and, as a result, an important part of the vector may be missed. SP is any sequence added as a dummy to prevent such deletion. This sequence may be selected at one's discretion. The length of SP is 100-1000 bp, preferably 300-400 bp. Any known sequence may be used as SP. For example, a part of rabbit -globin gene may be used.

The splice acceptor means a sequence that can be linked to the 3' end of an exon at the time of splicing.

The splice donor means a sequence that can be linked to the 5' end of an exon at the time of splicing.

IRES, called "internal ribosomal entry site", is a site on ribosome to which aminoacyl t-RNA is bound during protein synthesis (A site), and it is a sequence to allow translation to start in a CAP independent manner.

The marker gene is a gene that serves as a marker to indicate whether the vector of the invention could trap a target gene. Specific examples of marker genes include E. coli-derived -galactosidase gene (lacZ gene) or a fusion gene between lacZ gene and neomycin (G418) resistance gene (-geo gene), CAT gene, GFP gene, SV40 large T gene, neomycin resistance gene, puromycin resistance gene, hygromycin resistance gene, and blasticidin resistance gene.

The plasmid vector is used after gene trapping to isolate the endogenous gene by plasmid rescue. Plasmid rescue technique is a method for recovering adjacent regions of the plasmid (which is replicable in E. coli) integrated in a trap vector using a part of the plasmid. For example, when a genomic DNA segment is linked to the plasmid, a fragment consisting of the plasmid and the genomic DNA segment linked thereto is excised by restriction enzyme treatment. The excised fragment is made circular and introduced into E. coli, which is then propagated. As a result, the genomic DNA segment flanking the plasmid can be recovered. Specific examples of the plasmid vector include pBR322, pUC (pUC18, pUC19, pUC118, pUC119, etc.), pSP (pSP64, pSP65, etc.), and pGEM (pGEM-3, pGEM-4, pGEM3Z, etc.). In addition, supF, ampicillin resistance gene, origin of replication, or restriction sites for cloning (e.g. multicloning site) may be linked to the plasmid vector independently or in an appropriate combination.

The vector shown in (a) above is designated "U8". The basic part of U8 (SA-IRES-geo-pA: FIG. 7) is derived from pGT1.8IRESbetageo. This pGT1.8IRESbetageo contains mouse En-2 gene-derived splice acceptor, IRES and -geo. lox71 is inserted into the BglII site of this plasmid followed by SalI treatment to thereby provide a SalI fragment. On the other hand, plasmid pEBN-Seti is prepared by inserting into a vector (such as pUC19) a 180 bp SP sequence, loxP and poly(A) signal. The SalI fragment obtained above is inserted into the SalI site of this plasmid to produce U8. Thus, the structure of this trap vector is expressed as follows (from the 5' end, in this order): any sequence, splice acceptor, lox71, IRES, -geo, pA, loxP, pUC19, and any sequence (FIG. 7).

The vector shown in (b) above is designated "U8delta". U8delta is obtainable by deleting the splice acceptor from U8. This vector has a structure in which lox71 is linked before the reporter -geo and loxP after -geo. This vector was given such a structure because the intermediate IRES and -geo can be removed completely by transiently expressing Cre after the vector has been integrated. As a result, plasmid pUC is located close to the mouse endogenous gene which was located upstream of the plasmid. Thus, the mouse endogenous gene can be isolated easily.

The vector shown in (c) above is designated "pU-Hachi". This vector is composed of SA-lox71-IRES-M-loxP-pA-PV-SP. pU-Hachi vector is derived from pGT1.8IRES -geo, and contains SA sequence from mouse En-2 gene and -geo sequence linked to encephalomyocarditis virus-derived IRES sequence. A BamHI fragment of lox71 is inserted into the BglII site of pGT1.8IRES -geo. Then, a plasmid was constructed by inserting an SP sequence, a loxP sequence, and poly A addition signal from mouse phosphoglycerate kinase-1 (PGK) into a modified vector from which lacZ sequence has been removed. The SP sequence is used to protect the 3' end of the trap vector. pU-Hachi is obtainable by inserting a SalI fragment of SA-IRES-lox71- -geo into the SalI site of the above plasmid.

The vector shown in (d) above is designated "pU-12". This vector is composed of SA-lox71-IRES-M-loxP-puro-pA-PV-SP. In order to construct this pU-12 trap vector, first, the PGK poly(A) signal of pE3NSE7 is replaced with puromycin resistance gene+PGK poly(A) signal. Then, lox511 is inserted into the BglII site downstream thereof. Then, a SalI fragment of SA-IRES-lox71- -geo from pU-Hachi is inserted into the restriction site of the resultant plasmid to thereby obtain pU-12.

The vector shown in (e) above is designated "pU-15". This vector is composed of lox71-M-loxP-pA-lox2272-PV-lox511. "lox2272" is a mutant loxP in which the spacer sequence (gcatacat) is changed to ggatactt (i.e. the second base "c" has been changed to "g", and the seventh base "a" to "t"). "lox511" is a mutant loxP in which the spacer sequence (gcatacat) is changed to gtatacat (i.e. the second base "c" has been changed to "t"). Since lox511 and lox2272 have mutations in the spacer, they do not cause recombination with other loxP sequences such as wild-type loxP or lox71, though two lox511 sequences or lox2272 sequences cause recombination with each other. The order of lox2272 and lox511 in the vector may be changed. Either one may come first. (This will apply to other vectors using these mutants.)

The vector shown in (f) above is designated "pU-16". This vector is composed of lox71-IRES-M-loxP-pA-lox2272-PV-lox511, and is obtainable by inserting IRES between lox71 and -geo of pU-15.

The vector shown in (g) above is designated "pU-17". In this vector, lox71 is integrated in a region of SA. This vector may be constructed as follows. Briefly, a plasmid is constructed by inserting lox511, loxP, PGK poly(A) signal and lox2272 into, for example, pSP plasmid. Then, lox71 is inserted into SA in pU-Hachi followed by insertion of -geo in this order. This plasmid is ligated to the plasmid constructed above to thereby obtain pU-17.

The vector shown in (h) is designated "pU-18". Like pU-17, this vector also has lox71 integrated in SA. pU-18 is obtainable by inserting IRES between SA and -geo of pU-17.

The vector shown in (i) is composed of (lox71-integrated SA)-M-loxP-pA-lox2272-promoter-M-lox511-SD. This vector is obtainable by inserting a promoter and M in this order into pU-17 instead of PV and ligating SD after lox511. This vector has a promoter added thereto. This promoter is not particularly limited. Any promoter may be used. For example, bacteria- or yeast-derived promoters described later in the section of transformant preparation; RNA polymerase promoters such as SP6 RNA polymerase promoter. T7RNA polymerase promoter, T3RNA polymerase promoter; or mammal-derived promoters such as EF1 (elongation factor 1) promoter. PGK (glycerophosphate kinase) promoter, MC1 (polyoma enhancer/herpes simplex thymidine kinase) promoter may be enumerated.

2. Gene Trapping

Two-step gene trapping is performed using the vector prepared as described above.

The first step is conventional gene trapping. "Conventional gene trapping" means to introduce the above trap vector into ES cells and to trap an endogenous gene present inherently in the ES cells. By these procedures, the endogenous gene in the ES cells is disrupted. Using these ES cells, the knockout mice described later can be prepared. After isolation of the trapped endogenous gene (FIG. 8; "gene X"), subtle mutations are introduced into this gene in *E. coli* using site-specific mutagenesis or the like (FIG. 8; "gene X"). For the introduction of mutations into gene X, known techniques such as Kunkel method, gapped duplex method, etc. and methods based on these techniques may be used. For example, mutations are introduced by using a mutagenesis kit utilizing site-specific mutagenesis (e.g. Mutant-K or Mutant-G available from Takara Shuzo) or LA PCR in vitro Mutagenesis series kit (Takara Shuzo).

The second step gene trapping means to introduce into ES cells the mutated endogenous gene (gene X') ligated downstream of lox66. By these procedures, recombination occurs between the lox71 site of the trap vector introduced in the first step and the lox66 site of the vector introduced in the second step. As a result, the modified gene can be introduced into ES cells in the form of a cassette composed of [(lox71/66)-(gene X')-(loxP)] (FIG. 8).

According to these procedures, not only modified endogenous genes but also human genes may be introduced. Any gene may be introduced. In the present invention, this method is designated exchangeable gene trapping.

3. Screening for Trap Vector-Integrated Clones (ES Cells)

If a gene trap vector was introduced into ES cells and then neomycin resistant clones have been selected from the resultant cells, these clones are considered to have the trap vector integrated downstream of a mouse endogenous gene. DNA is extracted from these clones and analyzed by Southern blotting, to thereby select clones in which a single copy of the trap vector is integrated. The inventors have found that this selection method enables efficient selection of mouse gene-trapping clones. Therefore, this will be used as a screening system in the present invention.

(1) Isolation of Neomycin Resistant Clones

In the present invention, electroporation, microinjection or the like is used for introducing trap vectors into ES cells. For example, 100 g of trap vector is introduced into 3×107 TT2 ES cells suspended in 0.8 ml of phosphate buffer by electroporation (using a BioRad GenePulser at 800 V and 3 F), and the resultant cells are cultured in the presence of G418 (concentration: 200 g/ml). After 1 week, neomycin resistant clones are isolated.

The gene trap vector is integrated into the ES cell gnome at random. Therefore, mere introduction of the trap vector into ES cells does not necessarily mean integration into a gene. The vector may be integrated into a non-gene region. However, since the trap vector contains a drug resistance gene neo (neomycin resistance gene), those cells expressing this gene are neomycin (also called G418) resistant. In other words, those cells that survive in the presence of neomycin are expressing neomycin resistance gene. The neomycin resistance gene in the trap vector is expressed only when integrated downstream of a mouse gene which is being expressed in the ES cells. Thus, the expression of this neomycin resistance gene means that it has been integrated downstream of a certain gene.

(2) Selection of ES Clones by Integration Pattern

DNA is extracted from ES clones by conventional methods, and integration patterns are analyzed by Southern blotting or the like. When the Southern blot pattern appears as a single band, it can be judged that only one copy of the vector is integrated. Therefore, the DNA expressing that pattern is selected. These procedures are performed in order to select those clones in which isolation of mouse endogenous genes by plasmid rescue will be easy. Also, those clones which have become neomycin resistant with only one copy of the vector are trapping mouse endogenous genes at an extremely high probability.

4. Establishment of Trap Lines (Transgenic Animals) by Production of Chimeric Animals Chimeric animals are produced by standard methods (FIG. 9). The species of chimeric animals produced in the present invention is not particularly limited. For example, mouse, rat, guinea pig, rabbit, goat, sheep, pig, dog or the like may be enumerated. In the present invention, mouse is preferable because of its easy handling and propagation.

ES cells selected with neomycin are aggregated with animal derived-morulae (i.e. aggregates of ES cells and morulae are formed) to prepare chimeric animal embryos (e.g. those developed to blastocysts). The resultant embryo is transferred into the uterus of a foster female animal that has been brought into a pseudo-pregnant state by mating with a sterile male animal. If the animal is mouse, offspring will be born about 17 days after this transfer. Chimeric animals are selected from the offspring animals. Although those that have a high contribution of chimerism are likely to be germline chimeric animals, this can be confirmed by crossing such chimeric animals with normal animals.

Subsequently, chimeric animals are crossed with normal female animals to obtain F1 to thereby establish mutant animal lines. The following analysis is conducted only for those animals that have been established as trap lines (transgenic animals). Further, spermatozoa from F1 and two-cell stage embryos obtained by in vitro fertilization using the spermatozoa can be stored frozen by ultra-quick freezing technique.

(1) Analysis of Expression Patterns

F1 animals are crossed and then expression patterns in embryos (in the case of mouse, 9.5-day embryos) and adult animals are analyzed.

(2) Analysis of Phenotypes

For each of the established animal lines, phenotypes of heterozygous and homozygous animals are analyzed. This analysis is carried out by macroscopic observation, internal observation by anatomy, microscopic examination of tissue sections from each organs, examination of the skeletal system by X-ray photography, examination of behavior and memory, and blood examination.

(3) Isolation and Structural Analysis of the Trapped Gene and Preparation of Chromosome Map Trapped DNA is isolated from the trap clone, and the nucleotide sequence thereof is determined (as described later). Then, homology search is performed using the sequence information obtained. Consequently, the sequence of the trapped DNA is classified into one of the groups of known genes, ESTs (expressed sequence tags), unknown genes or repeats. If the DNA is an EST or unknown gene, a chromosome map can be prepared. Chromosome maps may be prepared by fluorescent in situ hybridization (FISH), association analysis using microsatellite probes or the like, or analysis of hybrid cells by irradiation. Once the position of the DNA on the chromosome has been determined, this position is compared with the positions of mutant genes in existing mutant mice to examine if the relevant position coincides with one of them.

(4) Construction of Database

For each of the established lines, database is prepared on expression patterns of the marker gene in embryos (in the case of mouse. 10-day embryos) and adult animals; phenotypes in F1 and F2 animals; the nucleotide sequence of the trapped endogenous DNA and, if the DNA is an EST or unknown gene, its position in the chromosome.

5. Knockout Animals

The knockout animal of the invention is an animal that has been treated so that the function of a specific gene is lost. The procedures of such treatment will be described below.

The animals that may be used in the present invention include mouse, rat, guinea pig, rabbit, goat, sheep, pig and dog. Preferably, mouse is used in the invention because of its easy handling and propagation.

A genomic DNA fragment containing an unknown gene is obtained by PCR from a genomic DNA prepared from animal ES cells or obtained from a genomic library. Then, this fragment is integrated into the trap vector of the invention. As a result of this operation, the function of the exons in the unknown gene is destroyed. In the trap vector, thymidine kinase (tk) gene or diphtheria toxin (DT) gene has been ligated in advance for negative selection. This trap vector is introduced into ES cells by electroporation or the like. The resultant cells are cultured in the presence of neomycin for positive selection and a nucleic acid analogue FIAU (fluoroiodoadenosyluracil) or diphtheria toxin for negative selection. Through these selections, only the trap vector-integrated ES cells remain. In these ES clones, the genes containing disrupted exons are knocked out. The resultant cells are transferred into the uterus of foster female animals. Then, chimeric animals are selected from offspring animals. By crossing these chimeric animals with normal animals, heterozygous animals are obtained. Then, homozygotes can be obtained through crossing between the heterozygotes.

In order to confirm that a knockout mouse is obtained, F1 mice are X-ray photographed and examined for bone abnormalities (e.g. changes in shape). Alternatively, this confirmation may be made by observing the presence or absence of abnormalities in the appearance of mice and by observing abnormalities in various tissues and organs at the time of anatomy. Also, the confirmation may be made by extracting RNA from tissues and analyzing the expression pattern of the relevant gene by Northern blotting. If necessary, blood samples may be taken and subjected to blood examination and serum biochemical examination.

6. Isolation of Genes, Construction of Recombinant Vectors and Preparation of Transformants (1) Isolation of Genes In the present invention, genes trapped as described above can be cloned and structurally analyzed.

Isolation of DNA from the trap clone may be performed by conventional techniques. For example, if cloning is performed using mRNA from the trap clone, first, total RNA is obtained from the trap clone by treating the clone with guanidine reagent, phenol reagent or the like. From the total RNA, poly(A+) RNA (mRNA) is obtained by affinity column method using, for example, oligo dT-cellulose or poly U-Sepharose containing Sepharose 2B as a carrier, or by batch method. Using this mRNA as a template, single-stranded cDNA is synthesized using oligo dT primers and a reverse transcriptase. Then, double-stranded cDNA is synthesized from the single-stranded cDNA. The thus obtained double-stranded cDNA is inserted into an appropriate expression vector (e.g. gt11) to thereby obtain a cDNA library.

The gene obtained as described above is subjected to sequencing. The sequencing may be performed by known techniques such as the chemical modification method of Maxam Gilbert or the dideoxy nucleotide chain termination method using DNA polymerase. Usually, the nucleotide sequence of the gene can be determined using an automated sequencer. When the 5' region or 3' region of the relevant cDNA is undetermined, the entire nucleotide sequence is determined by 5'-RACE or 3'-RACE. RACE (Rapid Amplification of cDNA Ends) is a well-known technique in the art (Frohman, M. A. et al. Methods Enzymol. Vol. 218, pp. 340-358 (1993)), and kits for performing RACE are commercially available (e.g. Marathon™ cDNA Amplification Kit; Clontech). Once the nucleotide sequence of the gene of the invention has been determined, the gene can be obtained by chemical synthesis or PCR using primers synthesized based on that sequence.

(2) Construction of Recombinant Vectors

A gene fragment of interest is purified and ligated to vector DNA. As the vector, any vector may be used such phage vector or plasmid vector. The technique to ligate DNA of interest to vectors is well known in the art (J. Sambrook et al. Molecular Cloning: A Laboratory Manual, Second Edition, Cold Spring Harbor Laboratory Press, 1989). Further, recombinant vectors are prepared from the resultant vector and introduced into E. coli or the like. Then, appropriate colonies are selected to prepare desired recombinant vectors.

(3) Transformants

The transformant of the invention can be obtained by introducing the recombinant vector of the invention into a host in such a manner that the gene of interest can be expressed. The host is not particularly limited as long as it can express the DNA of the invention. Specific examples of the host include bacteria, yeast, animal cells and insect cells.

When a bacterium such as E. coli is used as the host, it is preferred that the recombinant vector of the invention be capable of autonomous replication in the bacterium and yet be composed of a promoter, a ribosome binding sequence, the gene of the invention, and a transcription termination sequence. A gene that controls the promoter may also be included. Specific examples of E. coli include Escherichia coli K12 and DH1, and specific examples of Bacillus include Bacillus subtilis. As the promoter, any promoter may be used as long as it can direct the expression of the gene of interest in the host such as E. coli. For example. E. coli- or phage-derived promoters such as trp promoter, lac promoter, PL promoter and PR promoter may be used. An artificially designed and modified promoter such as tac promoter may also be used. As a method for introducing the recombinant vector into a host bacterium, any method for introducing DNA into bacteria may be used. For example, the method using calcium ions (Cohen, S. N. et al., Proc. Natl. Acad. Sci. USA, 69:2110-2114 (1972)), electroporation (Becker, D. M. et al., Methods. Enzymol., 194:182-187 (1990) or the like may be used.

When yeast is used as the host, Saccharomyces cerevisiae, Shizosaccharomyces pombe or the like may be used. As the promoter, any promoter may be used as long as it can direct the expression of the gene of interest in yeast. For example, gal1 promoter, gal10 promoter, heat shock protein promoter, MF1 promoter, PH05 promoter. PGK promoter. GAP promoter, ADH promoter and AOX1 promoter may be enumerated. As a method for introducing the recombinant vector into yeast, any method for introducing DNA into yeast may be used. For example, electroporation, the spheroplast method (Hinnen, A. et al., Proc. Natl. Acad. Sci. USA, 75:1929-1933 (1978), the lithium acetate method (Itoh, H., J. Bacteriol., 153: 163-168 (1983) or the like may be used.

When an animal cell is used as the host, COS cells, Vero cells, Chinese hamster ovary cells (CHO cells), mouse myeloma cells or the like may be used. As the promoter. SR promoter, SV40 promoter, LTR promoter, EF1 promoter, PGK promoter, MC1 promoter, or the like may be used. Alternatively, human cytomegalovirus early gene promoter or the like may be used. As a method for introducing the recombinant vector into an animal cell, electroporation, the calcium phosphate method, lipofection, or the like may be used.

When an insect cell is used as the vector, Sf9 cells, Sf21 cells or the like may be used. As a method for introducing the recombinant vector into an insect cell, the calcium phosphate method, lipofection, electroporation, or the like may be used.

BRIEF DESCRIPTION OF THE DRAWINGS

FIG. 2 is a diagram showing an outline of the construction of a trap vector and the gene trapping according to the invention.

FIG. 11 is a photograph showing a bending mutation in the tailbone in mouse.

BEST MODES FOR CARRYING OUT THE INVENTION

Figure 1:
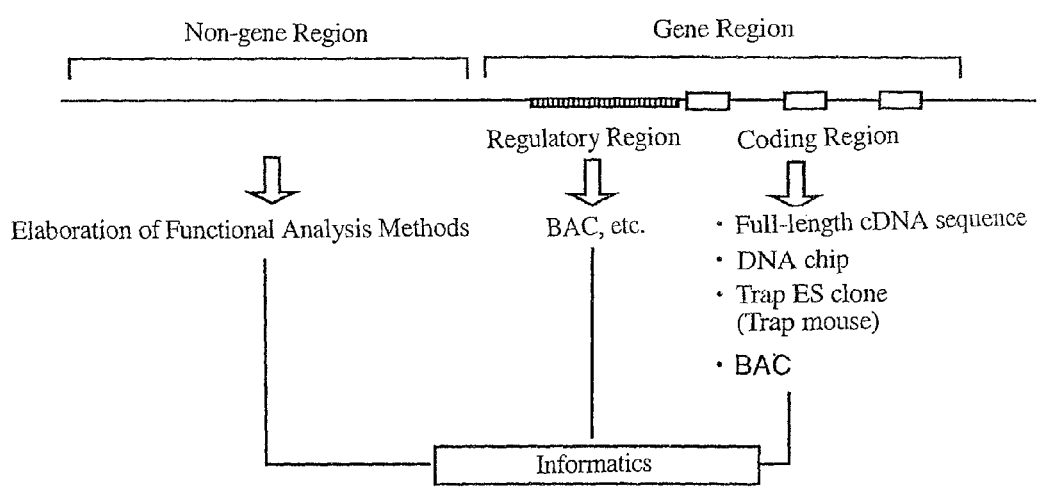
FIG. 1 is a diagram showing the concept of structural analysis in both gene region and non gene region.
Figure 3:
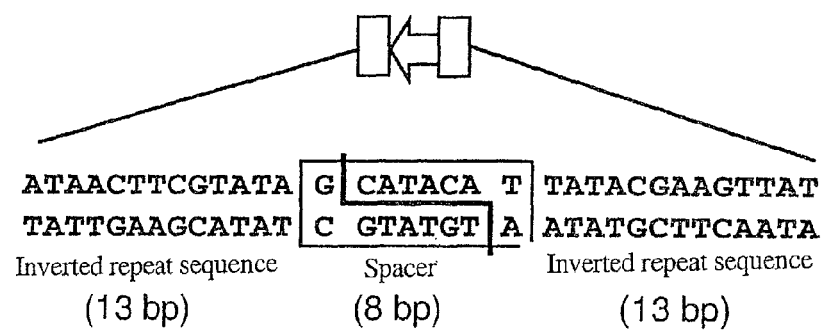
FIG. 3 is a diagram showing the structure of loxP (top sequence-SEQ ID NO: 3; bottom sequence-SEQ ID NO: 17).
Figure 4:
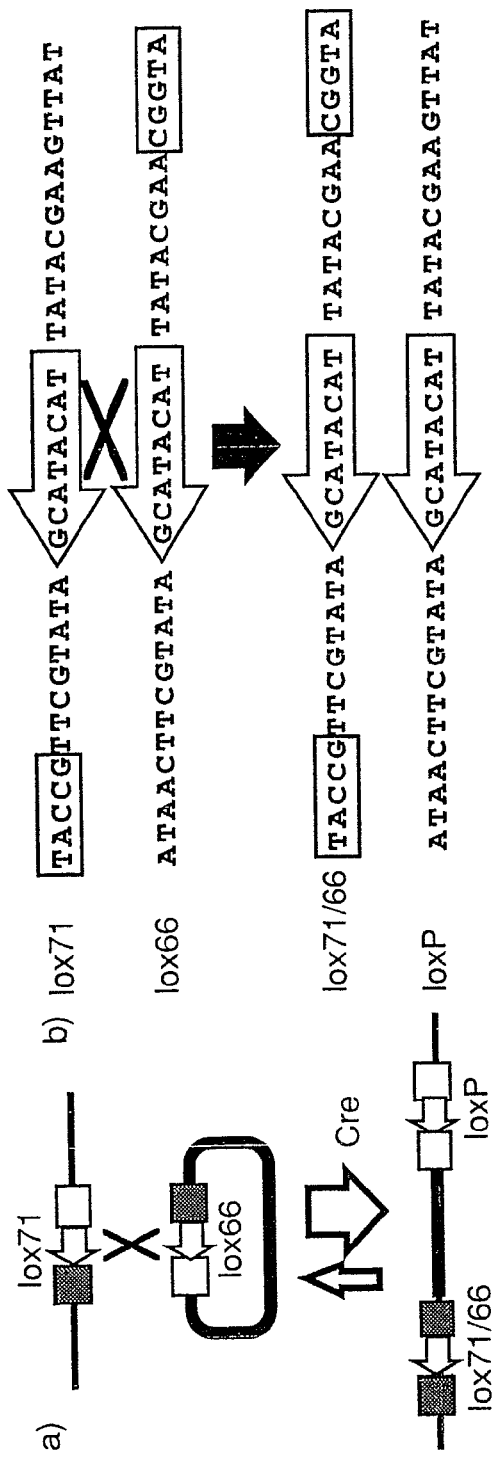
FIG. 4 is a diagram showing recombination between lox71 and lox66 (SEQ ID NOS: 15 (lox71), 16 (lox66), 6 (lox71/66), and 3 (loxP)).
Figure 5:
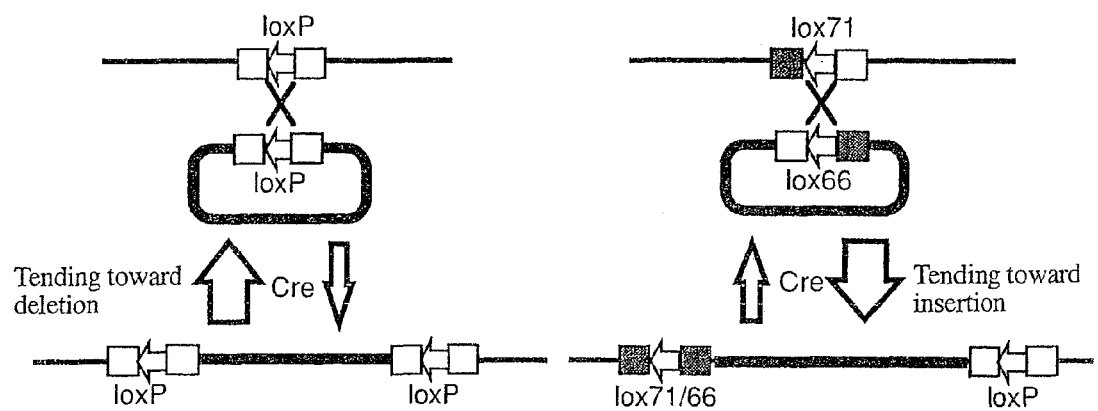
FIG. 5 is a diagram showing insertion of a DNA fragment when mutant loxP sequences are used.
Figure 6:
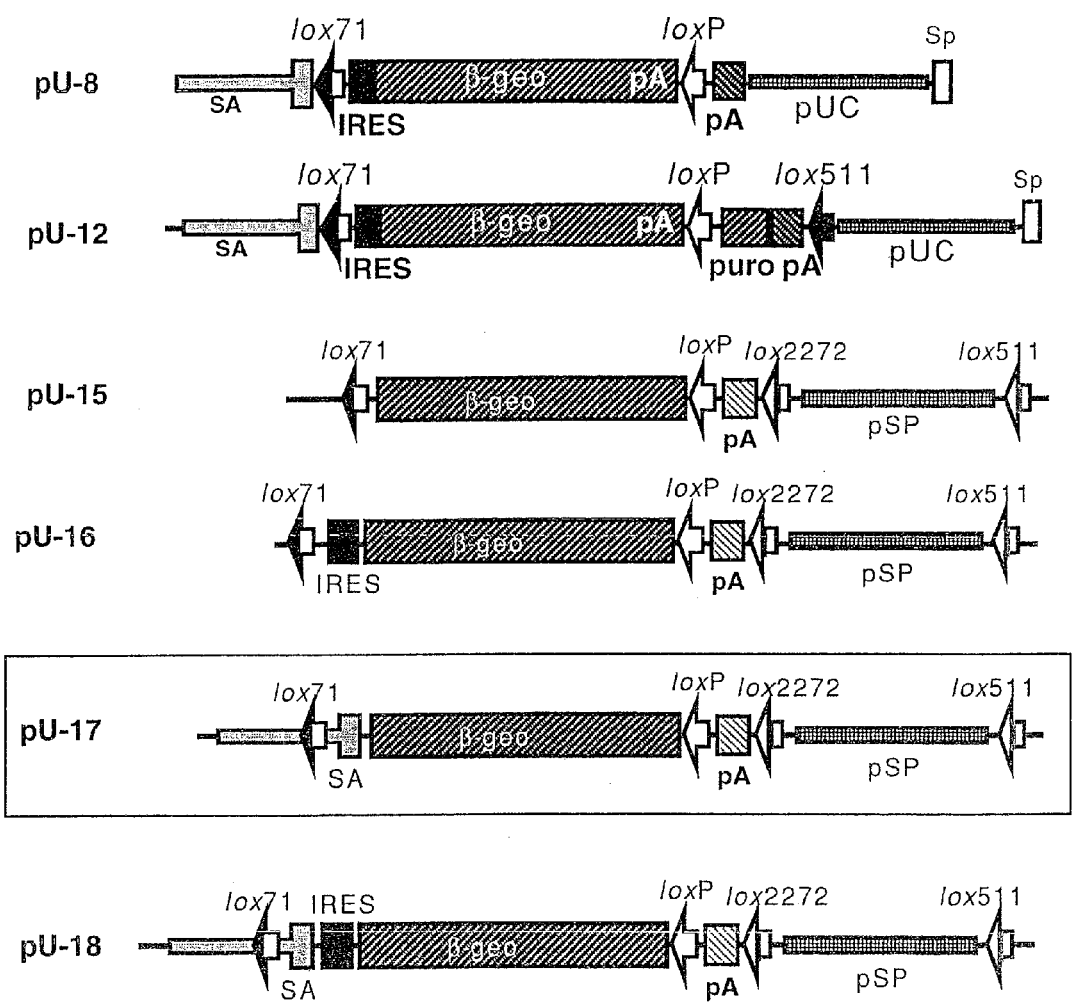
FIG. 6 is a diagram showing trap vectors of the invention.
Figure 7:
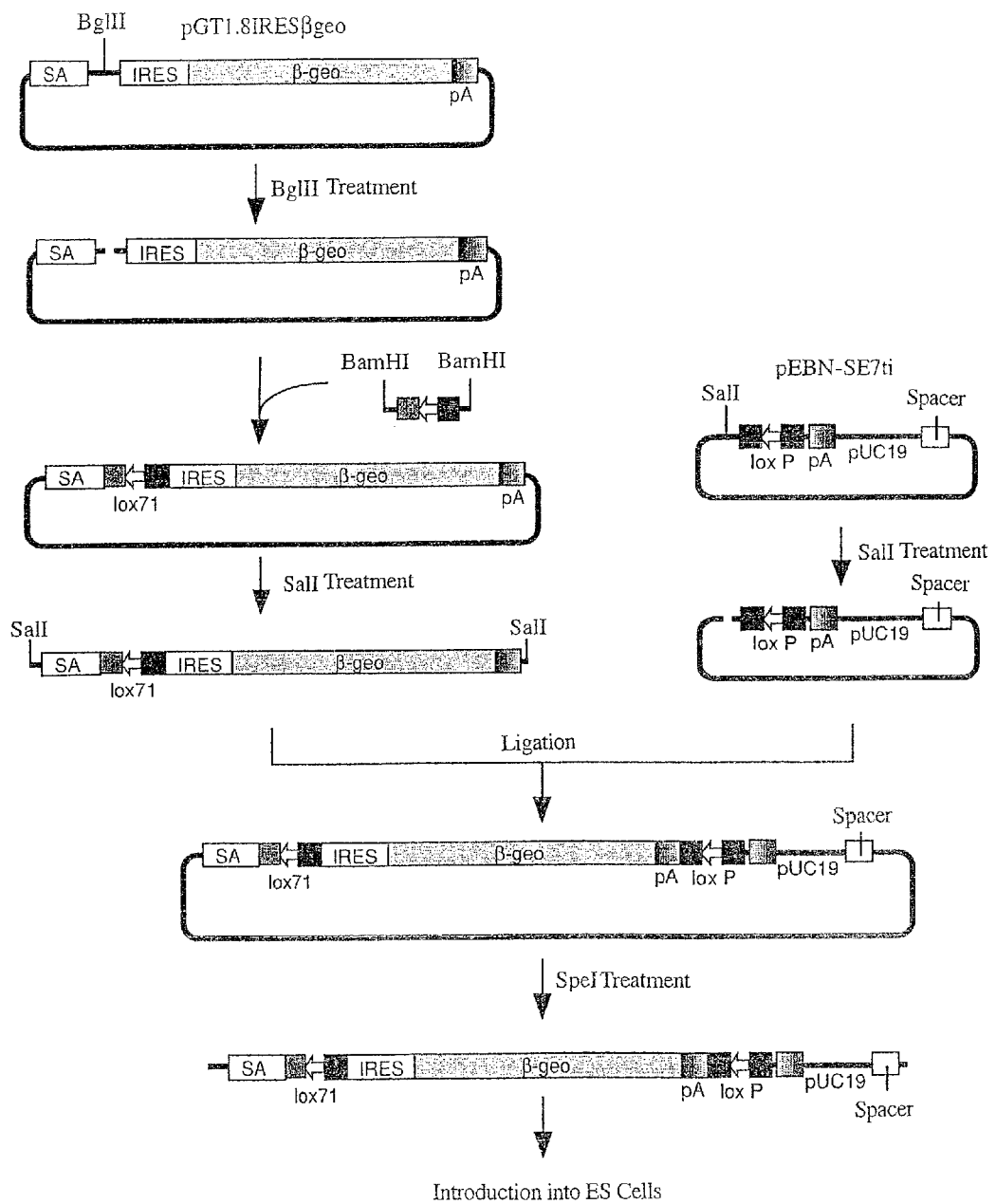
FIG. 7 is a flow chart showing the construction of a trap vector pU-Hachi.
Figure 8:
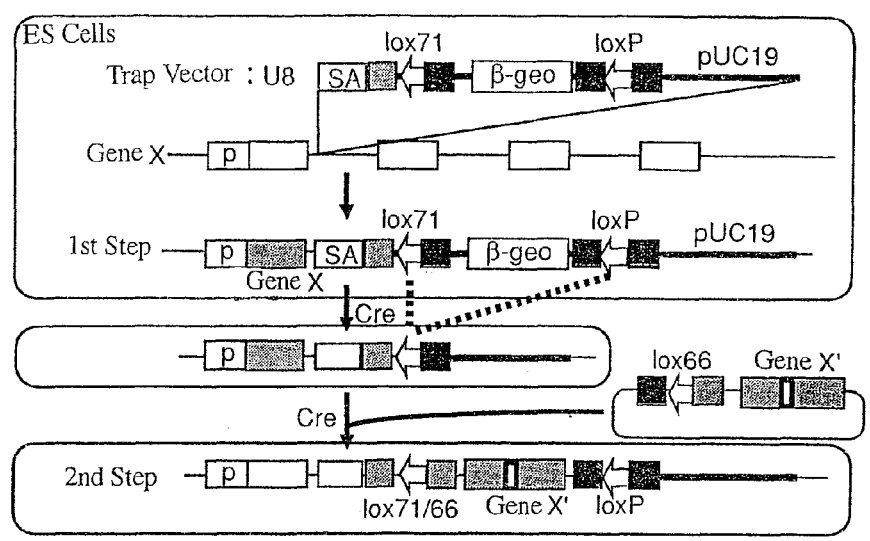
FIG. 8 is a diagram showing the two-step exchangeable gene trapping of the invention.
Figure 9:
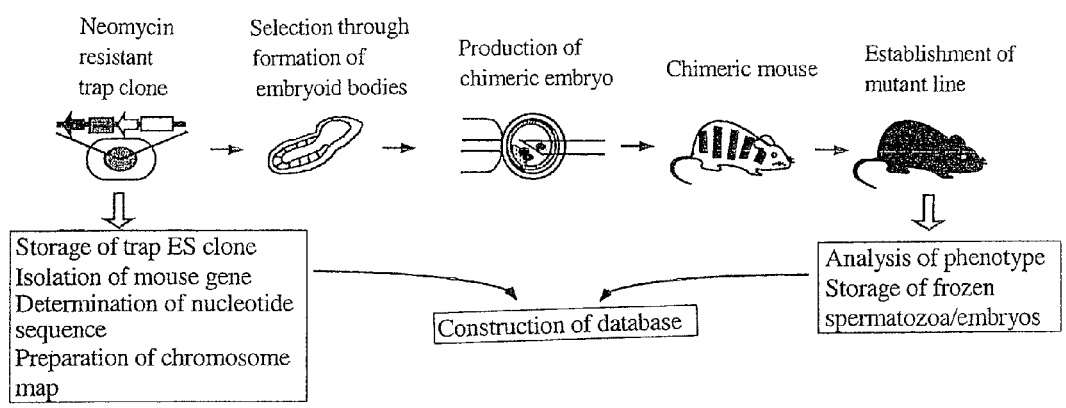
FIG. 9 is a diagram showing an outline of the establishment of trap lines by production of chimeric animals.
Figure 10:
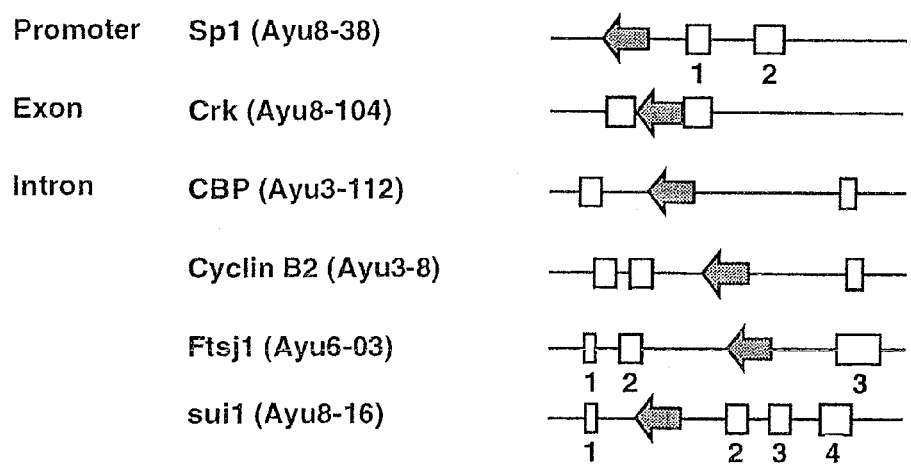
FIG. 10 is a diagram showing various positions of integration of trap vectors.

Hereinbelow, the present invention will be described in more detail with reference to the following Examples. It should be noted that the technical scope of the present invention is not limited by these Examples.

EXAMPLE 1

Construction of Varied-Type Gene Trap Vectors (1) Construction of pU-Hachi Trap Vector pU-Hachi vector is derived from pGT1.8IRES-geo, and contains SA sequence from mouse En-2 gene and β-geo sequence linked to encephalomyocarditis virus-derived IRES sequence. First, a BamHI fragment of lox71 is inserted into the BglII site of pGT1.8IRES -geo. Then, plasmid pEBN-SE7ti was constructed by inserting a 180 bp (SP) sequence (which is a part of rabbit globin gene), loxP sequence, and poly A addition signal from mouse phosphoglycerate kinase-1 (PGK) into a modified vector pUC19 from which lacZ sequence has been removed. The SP sequence was used to protect the 3' end of the trap vector. By inserting a SalI fragment of SA-IRES-lox71-β-geo into the SalI site of pEBN-SE7ti, pU-Hachi was obtained.

(2) Construction of pU-12 Trap Vector

In order to construct pU-12 trap vector, first, the PGK poly(A) signal of pE3NSE7 was replaced with puromycin resistance gene+PGK poly(A) signal. Then, lox511 was inserted into the BglII site downstream thereof to prepare a plasmid. By inserting a SalI fragment of SA-IRES-lox71-β-geo from pU-Hachi into the SalI site of the above plasmid, pU-12 was obtained.

(3) Construction of pU-17 Trap Vector

First, lox511, loxP, PGK poly(A) signal and lox2272 were inserted in this order into plasmid pSP73 (Promega) to construct pSP5PP2. Subsequently, pU-Hachi was cleaved at one of the two BamHI sites within SA located upstream of the other. The DNA fragment of pU-Hachi up to the upstream BamHI site in SA, lox71 sequence, the DNA fragment of pU-Hachi from the downstream BamHI site in SA to the KpnI site, and a NcoI-SalI fragment of β-geo were inserted in this order into pBluescriptII KS+ plasmid to construct pKS+ S71A geo. From this plasmid, an XbaI fragment of SA-β-geo containing lox71 was excised and inserted into the SpeI site of pSP5PP2 to thereby obtain pU-17.

EXAMPLE 2

Selection of ES Cell Clones

In the electroporation using pU-Hachi trap vector, 100 g of SpeI-digested DNA and $3\times10^7$ cells were used. Cells were suspended in 0.8 ml of PBS and electroporated using a Bio-Rad GenePulser at 800 V and 3 F. After 48 hours, the cells were cultured in the presence of 200 g/ml G418. This selection was maintained for 7 days. The resultant colonies were plated on 24-well plates for propagation and stored frozen. Trap clones were analyzed by Southern blotting to select those cell strains that exhibit patterns of single copy integration.

In order to remove β-geo sequence from the trap clone, pCAGGS-Cre (Araki, K. et al., Proc. Natl. Acad. Sci. USA, 92:160-164, 1995; Araki, K. et al., *Nucl. Acids Res.*, 25:868-872, 1997: Araki, K. et al., J. Biochem. Tokyo, 122: 977-982, 1997) was electroporated in a circular form. This electroporation was carried out under the same conditions as described above except that the number of cells was $1.5 \times 10^7$ and that the PBS volume was 0.4 ml.

One half of the thus treated cells were plated onto a 100 mm plate and grown for 48 hours. Then, the cells were re-plated onto 100 mm plates at $1 \times 10^3$ cells per plate for colony formation. After 1 week, colonies were picked up and expanded for DNA preparation.

For the co-electroporation experiments designed for targeted integration into the lox71 site of the trap vector, 20 g of each targeting plasmid (p66²IEGPPac, p66²INZPPac or p66PGKPac-5) and pCAGGS-Cre were used in circular forms.

Plasmid p66PGKPac-5 was constructed by inserting a lox66 fragment and PGK promoter-puromycin resistance gene coding sequence into pSP73 vector (Promega). Plasmid p66²IEGPPac was constructed from pSP73 vector (Promega), IRES sequence, EGFP gene (Clontech), PGK promoter, Pea gene and lox66 sequence. Plasmid p66²INZPPac was constructed by replacing the PGK gene in p66²IEGPPac with a lacZ gene fused to SV40 large T gene-derived nuclear localization signal.

Cells suspended in PBS ($1 \times 10^7$ cells/0.8 ml) were electroporated at 200 V and 950 F. After 48 hours, the cells were subjected to selection with puromycin at 2 g/ml for 3 days. Then, the cells were transferred into a normal medium. Nine days after the electroporation, colonies were picked up and expanded.

Embryoid bodies (EBs) were produced according to a known method (Abe, K., Niwa, H. et al., *Exp. Cell Res.* 229: 27-34, 1996) -galactosidase activity in ES cells and EBs was determined by staining with 5-bromo-4-chloro-3-indolyl -D-galactopyranoside (X-gal) as described (Glossier, A. and Zachgo, J., *Gene Targeting: A Practical Approach*, Joyner A. (ed.), Oxford University Press, Oxford, 1993, pp. 181-227).

Trap vector pU-Hachi was linearized and introduced into TT2 ES cells. As a result, 109 clones were isolated. Genomic DNA was prepared from each clone and subjected to Southern blotting using a pUC probe and at least 3 restricting enzymes to examine trap vector-integration patterns.

A single hand was confirmed in 69% of the clones. Since the presence of lox71 site is essential for the Cre-mediated integration, the presence was confirmed by Southern blotting using a lacZ probe and PstI digestion. As a result, it was found that lox71 was deleted in 10% of the clones (Table 4). The remaining 59% of the clones in which a single copy was integrated and yet lox71 site was maintained were selected for further analysis.

TABLE 4

| Total No. of clones tested | Single copy integration (%) | | | Multi-copy integration (%) | |
|---|---|---|---|---|---|
| | Clones retaining lox71 site | | | | |
| | Retaining plasmid replication origin | Without plasmid replication origin | Clones without lox71 site | 2-3 copies | 5 copies |
| □□□ □□□□□ | □□ □□□□ | □□ □□□□ | □□ □□□□ | □□ □□□□ | □ □□□ |

In order to evaluate the capture of endogenous genes by the trap vector, cells were stained with X-gal before and after the formation of embryoid bodies. As shown in Table 5, 97% of the tested clones exhibited -gal activity at a specific stage in differentiation. This means that pU-Hachi trap vector performs effective gene trapping comparable to the trapping of other IRES-β-geo vectors.

TABLE

| | Expression of β-geo | |
|---|---|---|
| Clone No. (%) | Undifferentiated ES Cells | Differentiated EBs (Day 8) |
| 26 (41) | + | + |
| 32 (50) | − | + |
| 4 (6) | + | − |
| 2 (3) | − | − |

EXAMPLE 3

Selection Frequency of Clones

In order to select those clones in which a single copy of the trap vector was integrated. DNA was extracted from the selected neomycin resistant clones and analyzed by Southern blotting.

Briefly, cells were lysed with SDS/proteinase K, treated with phenol/chloroform (1:1, vol:vol) twice, precipitated with ethanol, and then dissolved in TE buffer (10 mM Tris-HCl, pH 7.5/1 mM EDTA). Six micrograms of genomic DNA was digested with appropriate restriction enzymes, electrophoresed on 0.9% agarose gel and then blotted onto a nylon membrane (Boehringer Mannheim). Hybridization was performed using a DIG DNA Labeling and Detection Kit (Boehringer Mannheim).

For PCR analysis, DNA was subjected to 28 cycles of denaturation at 94, for 1 min, annealing at 55, for 2 min and extension at 72 for 2 min in the reaction solution described below.

The primers used in the PCR were as follows:

```
β-geo detection primers
                                            (SEQ ID NO: 7)
Z1 (forward):      5'-gcgttacccaacttaatcg-3'

(SEQ ID NO: 8)
Z2 (reverse):      5'-tgtgagcgagtaacaacc-3'

Primers for detecting the replication origin
in pUC vector
                                            (SEQ ID NO: 9)
Ori2 (forward):    5'-gccagtggcgataagtcgtgtc-3'

(SEQ ID NO: 10)
Ori3 (reverse):    5'-cacagaatcaggggataacgc-3'
```

| Reaction Solution | |
|---|---|
| 10 x PCR buffer | 2 1 |
| 10 mM dNTP | 0.2 1 |
| Forward primer (100 pmol/l) | 0.2 1 |
| Reverse primer (100 pmol/l) | 0.2 1 |
| AmpliTaq DNA polymerase (Perkin Elmer) | 0.2 1 |
| Total Volume (adjusted with sterilized distilled water) | 20 1 |

One half of the resultant FOR product was loaded onto agarose gel and analyzed.

Plasmid rescue (i.e. recovery of the trapped gene) was performed as described below.

Briefly, genomic DNA (20 g) was digested with appropriate restriction enzymes and ligated in a reaction volume of 400 l to obtain circular molecules. After phenol/chloroform extraction and ethanol precipitation, the DNA was suspended in 10 l of TE. Using one half of this DNA suspension, E. coli (STBL2: Life Technologies) was transformed by electroporation. The electroporation was performed according to the manual of BioRad GenePulser. The electroporated cells were incubated in 1 ml of Circle Grow medium (BIO 101) at 30 for 1 hour under agitation. Then, after concentration, the sample was plated on LB/agar plates followed by selection of plasmids with ampicillin. The rescued plasmids were analyzed by restriction mapping and sequencing. Nucleotide sequences were determined with Thermo Sequenase Fluorescent-Labeled Primer Cycle Sequencing Kit (Amersham).

As a result, as shown in Table 6, clones in which recombination occurred at a high frequency could be obtained.

TABLE 6

| Trap Clone | No. of subclones analyzed | No. of subclones in which recombination occurred | Recombination frequency (%) | Length of the 5' flanking region obtained by plasmid rescue (kb) | Length of the 3' flanking region obtained by plasmid rescue (kb) |
|---|---|---|---|---|---|
| Ayu8-003 | 23 | 15 | 65 | 75 | 53 |
| Ayu8-016 | 20 | 2 | 10 | 3.8 | 4.5 |
| Ayu8-025 | 23 | 16 | 70 | 1.8 | 6.5 |
| Ayu8-104 | 12 | 5 | 42 | 3.5 | 7 |
| Ayu8-108 | 12 | 6 | 50 | 5 | 6 |

EXAMPLE 4

Production of Chimeric Mice and Gene Analysis (1) Introduction of the Clone into Mice The trap ES clone was aggregated with ICR mouse-derived 8 cell stage embryos and cultured overnight. On the next day, aggregates of the ES cell and embryo that had developed to blastocysts were selected. Approximately 20 of these chimeric embryos were transferred into the uterus of a foster female mouse that was pre-mated with a sterile male mouse. Offspring mice were born about 17 days thereafter. Eight weeks after birth when they became sexually mature, these chimeric mice were crossed with normal female mice to obtain ES clone-derived F1 mice.

(2) Analysis of Phenotypes

The F1 mice were X-ray photographed, and the presence of absence of abnormalities in the bone was observed.

(3) Analysis of the Trapped Gene

Since the trapped gene must be forming a fusion mRNA with β-geo, the trapped gene was identified utilizing this presumption.

Briefly, mRNA was extracted from X-gal staining-positive tissues of F1 mice. From the resultant mRNA, single-stranded cDNA was synthesized with a Thermoscript RT-PCR system (GIBCO BRL) using sequences within the SA as primers. Subsequently, a cDNA fragment corresponding to the upstream region of the trapped gene that was linked to the exon of the SA in the vector was obtained using a 5'RACE system (GIBCO BRL). The resultant cDNA fragment was cloned into a plasmid vector and subjected to sequencing.

(4) Results

Table 7 shows one example of the results obtained from the analysis of trapped genes.

TABLE 7

| | Clone No. | Gene | Phenotype |
|---|---|---|---|
| 1 | Ayu8-R38 | Sp1 | |
| 2 | Ayu8-029 | PCM1 (pericentriol material 1) | |
| 3 | Ayu3-008 | Cyclin B2 | |
| 4 | Ayu6-003 | Homologue to the E. coli Ftsj1 gene | |
| 5 | Ayu8-003 | dynamin II | Death at embryonic stage |
| 6 | Ayu8-R16 | sui1 | |
| 7 | Ayu8-016 | Upstream region of hnRNP L | |
| 8 | Ayu8-019 | RNA polymerase 1 | |
| 9 | Ayu8-108 | importin β | |
| 10 | Ayu8-021 | Unknown | Kinky tail |

Among the genes obtained as described above, PCM1 gene was analyzed. As a result, sequences shown in SEQ ID NOS: 11 to 13 (5'RACE partial fragments) were obtained. These sequences matched with a part of the known PCM1 gene. Further, the mice obtained from Ayu8-021 clone exhibited a mutation of bending in the tail hone (kinky tail) (FIG. 11). This mutant gene fragment was sequenced to thereby obtain the sequence as shown in SEQ ID NO: 14.

All of the publications, patents and patent applications referred to in the present specification are incorporated herein by reference in their entirety.

Industrial Applicability

The present invention provides gene trap vectors and a method of gene trapping. According to the present invention, first, (1) knockout mice can be produced efficiently. In most cases, mouse genes are knocked out by the integration of the trap vector into genes. Therefore, if the trap vector-introduced ES cells are used, a mouse gene-knocked out mice can be produced. That is, knockout mice can be produced efficiently by selection of neomycin resistant clones and selection of those clones in which a single copy of the trap vector is integrated. According to conventional homologous recombination methods, one researcher can produce only 4 lines of knockout mice in one year at his/her best. According to the method of the invention, however, one researcher can establish as many as 240 lines in one year if for example, he/she establishes 6 lines per week and works 40 weeks a year. Thus, the method of the invention is 60 times more efficient than conventional methods.

(2) The method of the invention allows detailed analysis of gene functions.

In the method of gene trapping of the invention, it is possible to introduce mutations in advance into each part of a gene that seems to have a certain function, and integrate the resultant mutant genes into trap vectors. Then, the mutant gene-integrated trap vector can be introduced into mouse followed by analysis of the phenotype.

(3) The method of the invention allows the production of disease model mice which are closer to human.

According to the present invention, it is possible to create disease model mice which are closer to human than conventional models because a human gene having the same mutation as found in a human disease can be introduced into mice replacing the corresponding mouse gene.

Sequence Listing Free Text
SEQ ID NO: 1: synthetic DNA
SEQ ID NO: 2: synthetic DNA
SEQ ID NO: 3: synthetic DNA
SEQ ID NO: 4: synthetic DNA
SEQ ID NO: 5: synthetic DNA
SEQ ID NO: 6: homologous recombination sequence
SEQ ID NO: 7: synthetic DNA
SEQ ID NO: 8: synthetic DNA
SEQ ID NO: 9: synthetic DNA
SEQ ID NO: 10: synthetic DNA References
(1) Relating to Gene Trapping:
  1) Wurst, W. et al. Genetics 139: 889-899, 1995.
  2) Chowdhury, K. et al., Nucleic Acids Res. 25:1531-1536, 1997.
  3) Hicks, G. G. et al., Nature Genetics 16: 338-344, 1997.
  4) Zambrowicz, B. P. et al., Nature 392: 608-611, 1998.

(2) Relating to the Cre-loxP System
  1) Sauer, B. and Henderson, N. Proc. Nat. 1. Acad. Sci. USA 85: 5166-5170, 1988.
  2) Lakso, M. et al., Proc. Natl. Acad. Sci. USA 89: 6232-6236, 1992,
  3) Gu. H. et al., Independent control of immunoglobulin switch recombination at individual switch regions evidenced 1993.
  4) Albert, H. et al., Plant J. 7: 649-659, 1995.
  5) Schwenk. F. et al., Nucleic Acids Res. 23: 5080-5081, 1995.

(3) List of References relating to Gene Trapping
  1) Miyazaki, J. et al., Gene 79: 269-277, 1989.
  2) Niwa. H. et al. Gene 108: 193-200, 1991.
  3) Niwa, H. et al., J. Biochem, 113: 343-349, 1993.
  4) Niwa. H. et al. Gene 169: 197-201, 1996.
  5) Abe. K., Niwa. H. et al., Exp. Cell Res. 229: 27-34, 1996.
  6) Araki. K. et al. Nucleic Acid Res. 25: 868-872, 1997.
  7) Araki. K. et al., J. Biochem. 122: 977-982, 1997.
  8) Oike, Y. et al., Human Mol. Genet-In Press
  9) Oike. Y. et al., Blood in press

What is claimed is:

1. A method of gene trapping, comprising the steps of: introducing a trap vector into mouse embryonic stem cells, the trap vector comprising:
   1) a loxP sequence and a lox71 sequence, wherein the loxP sequence comprises in sequential order inverted repeat sequence 1, a spacer sequence, and inverted repeat sequence 2; wherein the loxP71 sequence comprises the nucleotide sequence showin in SEQ ID NO: 13; and wherein the trap vector is suitable for use in mammalian cells, or
   2) a loxP sequence and a lox66 sequence, wherein the loxP sequence comprises in sequential order inverted repeat sequence 1, a spacer sequence, and inverted repeat sequence 2, wherein the lox66 comprises the nucleotide sequence shown in SEQ ID NO: 16, and wherein the trap vector is suitable for use in mammalian cells,
   wherein the trap vector comprises a splice acceptor site and an internal ribosomal entry site;
   culturing the mouse embryonic stem cells;
   selecting those cells which exhibit a pattern of single copy integration of the trap vector; and isolating the trapped gene.

2. The method according to claim 1, wherein the trap vector comprises 1) the loxP sequence and the lox71 sequence.

3. The method according to claim 1, wherein the trap vector comprises 2) the loxP sequence and the lox66 sequence.

4. The method according to claim 1, wherein the trap vector further comprises a marker gene.

* * * * *

SEQUENCE LISTING

```
<160> NUMBER OF SEQ ID NOS: 17

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
taccgttcgt ata                                                          13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
tatacgaacg gta                                                          13

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
ataacttcgt atagcataca ttatacgaag ttat                                   34

<210> SEQ ID NO 4
<211> LENGTH: 13
<212> TYPE: DNA
<213> ORGANISM: Artificial Sequence
<220> FEATURE:
```

```
<223> OTHER INFORMATION: Description of Artificial Sequence:synthetic
      DNA

<400> SEQUENCE: 4
ataacttcgt ata                                                          13

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
tatacgaagt tat                                                          13

<210> SEQ ID NO 6
<211> LENGTH: 34
<212> TYPE: DNA
<213> ORGANISM: Artificial Sequence
<220> FEATURE:
<223> OTHER INFORMATION: Homologous recombination sequence

<400> SEQUENCE: 6
taccgttcgt atagcataca ttatacgaac ggta                                   34

<210> SEQ ID NO 7
<211> LENGTH: 19
<212> TYPE: DNA
<213> ORGANISM: Artificial Sequence
<220> FEATURE:
<223> OTHER INFORMATION: Z1 Forward primer used in PCR for B-geo
      detection

<400> SEQUENCE: 7
gcgttaccca acttaatcg                                                    19

<210> SEQ ID NO 8
<211> LENGTH: 18
<212> TYPE: DNA
<213> ORGANISM: Artificial Sequence
<220> FEATURE:
<223> OTHER INFORMATION: Z2 reverse primer used in PCR for B-geo
      detection

<400> SEQUENCE: 8
tgtgagcgag taacaacc                                                     18

<210> SEQ ID NO 9
<211> LENGTH: 22
<212> TYPE: DNA
<213> ORGANISM: Artificial Sequence
<220> FEATURE:
<223> OTHER INFORMATION: Ori2 forward primer used in PCR for detecting
      the replication origin region in pUC vector

<400> SEQUENCE: 9
gccagtggcg ataagtcgtg tc                                                22

<210> SEQ ID NO 10
<211> LENGTH: 21
<212> TYPE: DNA
<213> ORGANISM: Artificial Sequence
<220> FEATURE:
<223> OTHER INFORMATION: Ori3 reverse primer used in PCR for detecting
      the replication origin region in pUC vector
```

-continued

```
<400> SEQUENCE: 10
cacagaatca ggggataacg c                                               21

<210> SEQ ID NO 11
<211> LENGTH: 400
<212> TYPE: DNA
<213> ORGANISM: Mus musculus
<220> FEATURE:
<221> NAME/KEY: misc_feature
<222> LOCATION: (36)..(36)
<223> OTHER INFORMATION: n is a, c, g or t
<220> FEATURE:
<221> NAME/KEY: misc_feature
<222> LOCATION: (70)..(70)
<223> OTHER INFORMATION: n is a, c, g or t
<220> FEATURE:
<221> NAME/KEY: misc_feature
<222> LOCATION: (362)..(362)
<223> OTHER INFORMATION: n is a, c, g or t
<220> FEATURE:
<221> NAME/KEY: misc_feature
<222> LOCATION: (364)..(364)
<223> OTHER INFORMATION: n is a, c, g or t
<220> FEATURE:
<221> NAME/KEY: misc_feature
<222> LOCATION: (377)..(377)
<223> OTHER INFORMATION: n is a, c, g or t

<400> SEQUENCE: 11
agaaacttaa acagcggata aacttcagtg atttanatca gagaagtatt ggaagtgatt     60
ctcaaggtan agcaacagcg gctaacaaca aacgtcagct tagtgaaaac cgaaagccct   120 tcaactttt gcctatgcag attaatacta acaagagcaa ggatgctact gcaagtcttc    180
caaagagaga gatgacaacg tcagcacagt gcaaagagtt gtttgcttct gctctaagta   240 atgaccttt gcaaaactgt caatctctga agaagatggg agaggggagc ctgcatggga    300
aacaccagat tgtaagcagg cttgttcaat cctgactata ttactaaagc tagttctatg   360
cnanaagttt tgtaaanaaa atgaaagtct gcaatgttga                         400

<210> SEQ ID NO 12
<211> LENGTH: 416
<212> TYPE: DNA
<213> ORGANISM: Mus musculus
<220> FEATURE:
<221> NAME/KEY: misc_feature
<222> LOCATION: (37)..(37)
<223> OTHER INFORMATION: n is a, c, g or t
<220> FEATURE:
<221> NAME/KEY: misc_feature
<222> LOCATION: (363)..(363)
<223> OTHER INFORMATION: n is a, c, g or t
<220> FEATURE:
<221> NAME/KEY: misc_feature
<222> LOCATION: (392)..(392)
<223> OTHER INFORMATION: n is a, c, g or t
<220> FEATURE:
<221> NAME/KEY: misc_feature
<222> LOCATION: (401)..(401)
<223> OTHER INFORMATION: n is a, c, g or t
<220> FEATURE:
<221> NAME/KEY: misc_feature
<222> LOCATION: (403)..(403)
<223> OTHER INFORMATION: n is a, c, g or t

<400> SEQUENCE: 12
tcttctagct ttgcagcata aagcagagca agctatnagc tgtgatggat gactctgttg    60
ttacagaaac tacaggaagc ttatctggag tcagcatcac atctgaacta aatgaagaac   120
tgaatgattt aattcagcgt ttccataatc agcttcgtga ttctcagcct ccagctgttc   180
```

```
cagacaacag aagacaggca gaaagtcttt cattaactag agagatttct cagagcagaa    240
atccctcagt ttctgaacat ttacctgatg agaaagtaca gcttttttagc aaaatgagag    300 tactacagga aagaacaag aaatggacaa attagttggg agaacttcat aaccttcgag    360
atnagcatct gaacaactca tcatttgtgc cntcaacttc ncnccaaaga agtggg        416
```

```
<210> SEQ ID NO 13
<211> LENGTH: 484
<212> TYPE: DNA
<213> ORGANISM: Mus musculus
<220> FEATURE:
<221> NAME/KEY: misc_feature
<222> LOCATION: (33)..(33)
<223> OTHER INFORMATION: n is a, c, g or t
<220> FEATURE:
<221> NAME/KEY: misc_feature
<222> LOCATION: (48)..(48)
<223> OTHER INFORMATION: n is a, c, g or t
<220> FEATURE:
<221> NAME/KEY: misc_feature
<222> LOCATION: (54)..(54)
<223> OTHER INFORMATION: n is a, c, g or t
<220> FEATURE:
<221> NAME/KEY: misc_feature
<222> LOCATION: (89)..(89)
<223> OTHER INFORMATION: n is a, c, g or t
<220> FEATURE:
<221> NAME/KEY: misc_feature
<222> LOCATION: (244)..(244)
<223> OTHER INFORMATION: n is a, c, g or t
<220> FEATURE:
<221> NAME/KEY: misc_feature
<222> LOCATION: (257)..(257)
<223> OTHER INFORMATION: n is a, c, g or t

<400> SEQUENCE: 13
gtttctacac ctactgaaca gcagcagcca ttnagctcaa atccttnca gggnaaaaca    60 gagtatatgg cttttccaaa accctctgna aagcagttct tctcttggag cagaaaagca   120
aaggaatcaa gaaacagccc gaagaggaag ctgaaaacac taagacacca tggttatatg   180
atcaagaagg tggagtagaa aaaccatttt tcaagactgg atttacagag tctgtagaga   240
aagntacaaa atagtanccg caaaaatcaa ccagatacaa gcaggagaag acgtcggttt   300
gatgaagaat cccttggaaa gctttagcag tatgcctgat cctatagacc caacatcagt   360
aactaaaaca tttaaaacaa gaaaagcatc tgcccaggcc agcctggcct ctaaggacaa   420
aactcccaaa tcaaagagta agaagaggat tctactcagc tgaaaagtag agttaaaaat   480
attg                                                                 484
```

```
<210> SEQ ID NO 14
<211> LENGTH: 211
<212> TYPE: DNA
<213> ORGANISM: Mus musculus

<400> SEQUENCE: 14
ctgtctgtca ttgtcgttct cctttagaag gcagaaaaga aatgggaaga aaaaaggcaa    60
aatctggaac actataacgg aaaggagttc gagaagctcc tggaggaagc tcaggccaac   120
atcatgaagt caattccaaa cctggagatg cccccagctt ccagcccagt gtcaagggga   180
gatgcggcag gggataagct ggagctgtca g                                   211
```

```
<210> SEQ ID NO 15
<211> LENGTH: 34
<212> TYPE: DNA
<213> ORGANISM: Artificial Sequence
<220> FEATURE:
```

-continued

<223> OTHER INFORMATION: Description of Artificial Sequence:synthetic
      DNA

<400> SEQUENCE: 15
taccgttcgt atagcataca ttatacgaag ttat                                34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 16
ataacttcgt atagcataca ttatacgaac ggta                                34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 17
tattgaagca tatcgtatgt aatatgcttc aata                                34